(12) United States Patent
Goodlett et al.

(10) Patent No.: US 6,829,539 B2
(45) Date of Patent: Dec. 7, 2004

(54) METHODS FOR QUANTIFICATION AND DE NOVO POLYPEPTIDE SEQUENCING BY MASS SPECTROMETRY

(75) Inventors: David R. Goodlett, Seattle, WA (US); Andrew Keller, Seattle, WA (US)

(73) Assignee: The Institute For Systems Biology, Seattle, WA (US)

(*) Notice: Subject to any disclaimer, the term of this patent is extended or adjusted under 35 U.S.C. 154(b) by 73 days.

(21) Appl. No.: 09/835,072

(22) Filed: Apr. 13, 2001

(65) Prior Publication Data

US 2002/0168682 A1 Nov. 14, 2002

(51) Int. Cl.$^7$ .......................... G01N 33/48; C12Q 1/68
(52) U.S. Cl. ............................................ 702/20; 435/6
(58) Field of Search ................................ 702/20; 435/6

(56) References Cited

FOREIGN PATENT DOCUMENTS

| EP | 0887646 A1 | 12/1998 |
|---|---|---|
| WO | WO93/24834 | 12/1993 |

OTHER PUBLICATIONS

Bruce et al., "High–Mass–Measurement Accuracy and 100% Sequence Coverage of Enzymatically Digested Bovine Serum Albumin from an ESI–FTICR Mass Spectrum," Anal. Chem. 71:2595–2599 (1999).
Berndt et al., "Reliable automatic protein identification from matrix–assisted laser desorption/ionization mass spectrometric peptide fingerprints," Electrophoresis, 20:3521–3526 (1999).
Chen et al., "A dynamic programming approach to de novo peptide sequencing via tandem mass spectrometry," Proceedings of the Eleventh Annual ACM–SIAM Symposium on Discrete Algorithms, San Francisco 389–398 (2000).
Dančik et al., "De novo peptide sequencing via tandem mass spectrometry," J. Comp. Biol., 6:327–342 (1999).
Goodlett et al., "Protein identification with a single accurate mass of a cysteine–containing peptide and constrained database searching," Anal. Chem., 72:1112–1118 (2000).
Gygi et al., "Quantitative analysis of complex protein mixtures using isotope–coded affinity tags," Nature Biotechnology, 17:994–999 (1999).
Horn et al., "Automated de novo sequencing of proteins by tandem high–resolution mass spectometry," Proc. Natl. Acad. Sci. USA, 97:10313–10317 (2000).
Keough et al., "A method for high–sensitivity peptide sequencing using postsource decay matrix–assisted laser desorption ionization mass spectrometry," Proc. Natl. Acad. Sci. USA., 96:7131–7136 (1999).

Nicola et al., "Automation of data collection for matrix–assisted laser desorption/ionization mass spectrometry using a correlative analysis algorithm," Anal. Chem., 71:3213–3219 (1998).
Pevzner et al., "Efficiency of database search for identification of mutated and modified proteins via mass spectrometry," Genome Research, 11:290–299 (2001).
Pevzner et al., "Mutation–tolerant protein identification by mass spectrometry," J. Comp. Biol., 7(6;:777–787 (2000).
Sechi and Chait, "A method to define the carboxyl terminal of proteins," Anal. Chem., 72:3374–3378 (2000).
Sechi and Chait, "Modification of cysteine residues by alkylation. A tool in peptide mapping and protein identification," Anal. Chem., 70:5150–5158 (1998).
Wilm et al., "De novo sequencing of proteins with mass spectrometry using the differential scanning technique," Proteome and Protein Analysis, (Springer) 65–79 (2000).

Primary Examiner—Marianne P. Allen
Assistant Examiner—Channing S. Mahatan
(74) Attorney, Agent, or Firm—McDermott Will & Emery LLP

(57) ABSTRACT

The invention provides a method of determining an amino acid sequence of a parent polypeptide. The method consists of: (a) obtaining mass spectra of two or more differentially labeled polypeptide fragments of a parent polypeptide; (b) assigning a mass and a weighting characteristic to two or more paired signals having a difference in mass corresponding to an integer value of said differential label, the weighting characteristic combining properties of each signal within said paired signals; (c) selecting from the mass spectra a paired signal having the assigned mass and a weighting characteristic distinguishable from non-peptide signals, the assigned mass indicating the mass of a polypeptide fragment within the spectra; (d) determining the difference in mass of the polypeptide fragments; (e) assigning the mass differences a satisfying amino acid name, and (f) orienting the assigned amino acid names. Also provided is a method of determining the amino acid sequence of a polypeptide. The method consists of: (a) constructing a graph from mass spectra of two or more differentially labeled polypeptides, the graph comprising a node with mass m, number of labels n, intensity i, and mass differential of labels δ; (b) creating a node corresponding to a paired signal having masses of about m and about m+nδ, and (c) adding a labeled weighted directed edge to the graph between any two nodes corresponding to a mass of an amino acid, the labeled weighted directed edge combining properties of the paired signals.

29 Claims, 3 Drawing Sheets

SEQUENCE LISTING

<160> NUMBER OF SEQ ID NOS: 14

<210> SEQ ID NO 1
<211> LENGTH: 10
<212> TYPE: PRT
<213> ORGANISM: Homo sapiens

<400> SEQUENCE: 1

Gln Asp Val Asp Asn Ala Ser Leu Ala Arg
1               5                   10

<210> SEQ ID NO 2
<211> LENGTH: 7
<212> TYPE: PRT
<213> ORGANISM: Homo sapiens

<400> SEQUENCE: 2

Gln Asp Val Asp Asn Ala Ser
1               5

<210> SEQ ID NO 3
<211> LENGTH: 9
<212> TYPE: PRT
<213> ORGANISM: Homo sapiens

<400> SEQUENCE: 3

Gln Gln Tyr Glu Ser Val Ala Ala Lys
1               5

<210> SEQ ID NO 4
<211> LENGTH: 13
<212> TYPE: PRT
<213> ORGANISM: Homo sapiens

-continued

```
<400> SEQUENCE: 4

Gln Glu Tyr Asp Glu Ser Gly Pro Ser Ile Val His Arg
 1               5                  10

<210> SEQ ID NO 5
<211> LENGTH: 8
<212> TYPE: PRT
<213> ORGANISM: Homo sapiens

<400> SEQUENCE: 5

Gln Glu Tyr Asp Glu Ser Gly Pro
 1               5

<210> SEQ ID NO 6
<211> LENGTH: 10
<212> TYPE: PRT
<213> ORGANISM: Homo sapiens

<400> SEQUENCE: 6

Ala Gly Phe Ala Gly Asp Asp Ala Pro Arg
 1               5                  10

<210> SEQ ID NO 7
<211> LENGTH: 16
<212> TYPE: PRT
<213> ORGANISM: Homo sapiens

<400> SEQUENCE: 7

Ser Tyr Glu Leu Pro Asp Gly Gln Val Ile Thr Ile Gly Asn Glu Arg
 1               5                  10                  15

<210> SEQ ID NO 8
<211> LENGTH: 9
<212> TYPE: PRT
<213> ORGANISM: Homo sapiens

<400> SEQUENCE: 8

Pro Asp Asn Ala Val Ile Thr Ile Gly
 1               5

<210> SEQ ID NO 9
<211> LENGTH: 11
<212> TYPE: PRT
<213> ORGANISM: Homo sapiens

<400> SEQUENCE: 9

Leu Leu Leu Leu Gly Ala Gly Glu Ser Gly Lys
 1               5                  10

<210> SEQ ID NO 10
<211> LENGTH: 8
<212> TYPE: PRT
<213> ORGANISM: Homo sapiens

<400> SEQUENCE: 10

Leu Leu Leu Leu Gly Ala Gly Glu
 1               5

<210> SEQ ID NO 11
<211> LENGTH: 12
<212> TYPE: PRT
<213> ORGANISM: Homo sapiens

<400> SEQUENCE: 11
```

```
Gly Asn Leu Gln Ile Asp Phe Ala Asp Pro Ser Arg
1               5                   10

<210> SEQ ID NO 12
<211> LENGTH: 5
<212> TYPE: PRT
<213> ORGANISM: Homo sapiens

<400> SEQUENCE: 12

Ile Asp Phe Ala Asp
1               5

<210> SEQ ID NO 13
<211> LENGTH: 11
<212> TYPE: PRT
<213> ORGANISM: Homo sapiens

<400> SEQUENCE: 13

Asp Leu Glu Ala His Ile Asp Ser Ala Asn Lys
1               5                   10

<210> SEQ ID NO 14
<211> LENGTH: 7
<212> TYPE: PRT
<213> ORGANISM: Homo sapiens

<400> SEQUENCE: 14

Asp Leu Glu Ala His Ile Asp
1               5
```

METHODS FOR QUANTIFICATION AND DE NOVO POLYPEPTIDE SEQUENCING BY MASS SPECTROMETRY

BACKGROUND OF THE INVENTION

This invention relates generally to proteomics and, more specifically to de novo sequencing of polypeptides using mass spectrometry.

Proteomics can be described as the study of proteins expressed by a given cellular state, and like genomics, it is a global rather than a hypothesis driven science. Questions for study are not asked in series, such as which protein causes a given biological activity or effect, but rather in parallel, such as how do all of the expressed proteins in a given cell describe that cell. The use of mass spectrometry in proteomic studies has been employed as part of a global comparison of proteins that seeks to define the proteins characteristic of a state or to determine differences between states. An example would be the comparison of proteomes from cancerous versus normal cells with the intent of discovering a protein or proteins that are associated with cancer.

Mass spectrometry methods have been employed as a descriptive science to catalogue or compare proteins that represent a given cellular condition. Additionally, mass spectrometric methods have also been employed for determining the relative abundance of proteins expressed between two different biological samples. These methods allow the changes in protein expression between cells in different conditions or environments to be studied on a global scale so that information on protein expression can be gathered on multiple proteins in a single experiment. Assessing the relative abundance of proteins between different conditions has been based on differential mass labeling of proteins with stable isotopes either in vitro or in vivo. Mass spectrometry data from these experiments can also be used to search protein databases in hopes of identifying proteins within the sample. However, additional information about the samples, such as the correct sequence of proteins within the sample, is not available.

Numerous drawbacks exist which hinder the accuracy or efficiency of sequence identification using database searching. For example, protein identity can not be determined for proteins whose sequence is not in a database, for example, because the genome from which the protein is derived might not have been sequenced yet. In addition, the increasing complexity of these databases can lead to several possible protein identifications for each polypeptide fragment making it difficult to determine the true protein identity with confidence. Furthermore, database searching is limited in that this method can not accurately detect mutations or post-translational modifications in proteins. Almost all protein sequences are post-translationally modified, and as many as 200 types of covalent modifications of amino acid residues are known. Post-translational modifications of proteins are often important for biological activity.

Mass spectrometry has been used to determine the amino acid sequence of proteins of interest without searching a database through a method called de novo sequencing. In this method, the difference in mass of mass spectrometry peaks is correlated to the mass of amino acids that make up the polypeptide sequence. One limitation of mass spectrometry de novo sequencing methods is that the mass spectrometry data needs to be of high quality so that polypeptide mass spectrometry signals can be distinguished over non-peptide signals. High thorough-put proteomics experiments, and experiments determining the relative mass of polypeptides between two samples, have not generated mass spectrometry data of sufficient quality for de novo sequence determination. Also instruments with this capability are currently available in only a few laboratories since they are expensive and need highly skilled operators. Another limitation of mass spectrometry de novo sequencing methods is that polypeptides must be labeled in such a way that directionality can be assigned to the sequence. It is important to know whether a given fragment ion results from charge retention on the amino- or carboxyl-terminus in order to determine orientation of the sequence.

Thus, there exists a need for efficient and reliable de novo sequencing from mass spectrometry data. The present invention satisfies this need and provides related advantages as well.

SUMMARY OF THE INVENTION

The invention provides a method of determining an amino acid sequence of a parent polypeptide. The method consists of (a) obtaining mass spectra of two or more differentially labeled polypeptide fragments of a parent polypeptide; (b) assigning a mass and a weighting characteristic to two or more paired signals having a difference in mass corresponding to an integer value of said differential label, the weighting characteristic combining properties of each signal within said paired signals; (c) selecting from the mass spectra a paired signal having the assigned mass and a weighting characteristic distinguishable from non-peptide signals, the assigned mass indicating the mass of a polypeptide fragment within the spectra; (d) determining the difference in mass of the polypeptide fragments; (e) assigning the mass differences a satisfying amino acid name, and (f) orienting the assigned amino acid names. Also provided is a method of determining the amino acid sequence of a polypeptide. The method consists of: (a) constructing a graph from mass spectra of two or more differentially labeled polypeptides, the graph comprising a node with mass m, number of labels n, intensity i, and mass differential of labels $\delta$; (b) creating a node corresponding to a paired signal having masses of about m and about m+n$\delta$, and (c) adding a labeled weighted directed edge to the graph between any two nodes corresponding to a mass of an amino acid, the labeled weighted directed edge combining properties of the paired signals.

DETAILED DESCRIPTION OF THE INVENTION

Figure 1:
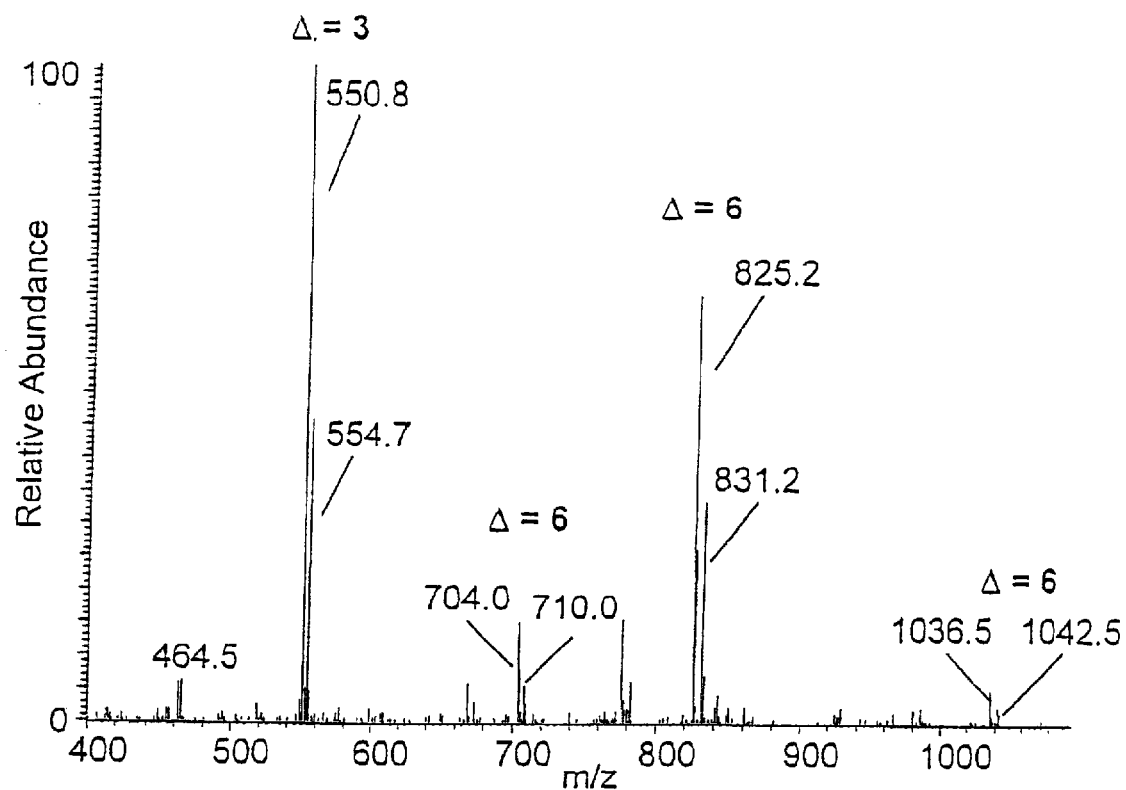
FIG. 1 shows the mass spectrum of myoglobin tryptic peptides esterified with d0- and d3-methanol.

This invention is directed to methods for determining the amino acid sequence of a polypeptide using mass spectrometry of differentially labeled polypeptides. The methods of the invention are applicable to proteome analysis of complex mixtures and allow rapid and efficient determination of the sequence of a polypeptide in a sample. The methods are based on comparisons of mass spectra from polypeptide samples or mixtures that have been labeled differentially according to mass. One advantage of the methods of the invention is that mass spectra data of differentially labeled polypeptide samples deposited in databases can be analyzed to determine, de novo, a particular polypeptide amino acid sequence.

Another advantage of the methods of the invention is that they allow de novo sequence determination of a polypeptide from low quality mass spectra such as those generated from proteomics studies. Moreover, quantitation can be performed together with de novo sequencing in a single study by using the same data without manipulation of the experimental procedures or data set. Therefore, the methods of the invention are applicable to a wide variety of qualitative and quantitative settings without special instrumentation or implementation procedures.

The methods of the invention use a predetermined or known mass differential between labels to augment the identification and selection of sample signals over background noise. The differential mass labels enhance the selection of mass spectra peaks corresponding to the polypeptide sample compared to non-polypeptide background peaks. Additional advantages are provided when a polypeptide is differentially labeled at both a terminus and at one or more internal sites. A terminal label aids orientation and ordering of assigned amino acids into sequence and the internal labels increase confidence that the correct signals are being selected.

In one embodiment, specific amino acid sequence was determined by mass spectrometry of differentially labeled polypeptides. Briefly, two samples were differentially labeled using isotopic methyl-esterification with either d0- or d3-methanol. This chemistry converts carboxylic acids, such as those present in the side chains of glutamic and aspartic acid and at the carboxyl-terminus to corresponding methyl esters. The result is that one sample contains a light mass label and the other contains a heavy mass label. Spectra were obtained for both the light and heavy labeled polypeptides and compared to identify fragment ions of the parent polypeptides to be sequenced. Peaks within the two spectra containing mass differences corresponding to a multiple of the mass label are identified as the polypeptide fragments. The mass difference corresponds to the number of labels in the polypeptide fragment, correlating with polypeptide length and enhancing the identification of specific polypeptide signals over non-polypeptide background signals. The carboxyl terminal label further augments de novo sequence analysis by orienting the mass signals for identification of y- and b-ions in the spectra and providing directionality for sequence determination. Once mass differences have been determined for the various fragments of a polypeptide, amino acids can be assigned and oriented into the corresponding sequence. The methods of the invention also provide a method for de novo sequence determination and this method can be automated to allow for rapid and efficient determination of polypeptide sequences.

As used herein, the term "polypeptide" is intended to mean two or more amino acids covalently bonded together. A polypeptide of the invention therefore includes small polypeptides having a few or several amino acids as well as large polypeptides having several hundred or more amino acids. Usually, the covalent bond between the two or more amino acid residues is an amide bond. However, the amino acids can be joined together by various other means known to those skilled in the peptide and chemical arts. Therefore, the term polypeptide is intended to include molecules which contain, in whole or in part, non-amide linkages between amino acids, amino acid analogs, and mimetics. Similarly, the term also includes cyclic polypeptides and other conformationally constrained structures. A polypeptide can also be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

A modification of a polypeptide can also include non-naturally occurring derivatives, analogues and functional mimetics thereof generated by, for example, chemical synthesis. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

A specific example of a polypeptide derivative includes modification of sulfhydryl groups to attach affinity reagents such as an ICAT™ type reagent. Another specific example of a modification of a polypeptide includes modification of polypeptides in a sample with a moiety having a stable isotope. For example, two different polypeptide samples can be separately labeled with moieties that are isotopically distinct, and such differentially labeled samples or polypeptides can be compared. Modification of polypeptides with stable isotopes can be used for both quantitating the relative amount of one or more individual polypeptides in a sample and for determining the amino acid sequence of one or more individual polypeptides by de novo mass sequencing.

As used herein, the term "fragment" when used in reference to a polypeptide or parent polypeptide is intended to mean any truncated or smaller mass form, corresponding to either carboxyl-terminal, amino-terminal, or both regions, of a reference polypeptide or parent polypeptide. Accordingly, a deletion of a single amino acid from the carboxyl- or amino-terminus is considered a fragment of a parent polypeptide. The term fragment therefore includes deletion of amino acids at the amino- and/or carboxyl-terminus as well as modifications where, for example, an amino acid side chain is removed but the peptide bond remains. A fragment includes a truncated polypeptide that is generated, for example, by polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation. Furthermore, a fragment can also result from multiple cleavage events such that a truncated polypeptide resulting from one cleavage event can be further truncated by additional cleavage events.

As used herein, the term "label" is intended to mean any moiety that can be attached to a polypeptide that results in a change in mass of that polypeptide. The label can be bound to the polypeptide either covalently or non-covalently. In addition, the label can be specifically bound to the polypeptide, for example through covalent attachment to a specific amino acid, or can be non-covalently bound to the polypeptide. The change in mass of the polypeptide due to the label should be within the sensitivity range of the instrument selected for mass determination. In addition, one skilled in the art will know or can determine the appropriate mass of a label for polypeptides of different sizes and different compositions. For example, large mass labels will enhance the accuracy of detection of any size polypeptide. Moreover, when using heavy and light mass labels, a mass difference as small as between about 1–3 mass units can be used or as large as greater than about 10 mass units. Similarly, mass differences between about 4–10 mass units can similarly be used in the de novo sequencing methods of the invention.

As used herein, the term "differential label" when referring to a polypeptide is intended to mean that the polypeptide has been modified to exist in two or more states that can be physically distinguished from each other based on mass. Therefore, the term describes two molecular species of a reference polypeptide or fragment that differs only by the number or weight of a mass label. The chemistries of the labels between the two or more mass states can be the same so that the only difference between the differently labeled reference polypeptides is the mass. Therefore, ionization and cleavages in the mass spectrometer will be the same or similar. Alternatively, the chemistries can be known or determined such that mass spectrum signals resulting from differentially labeled polypeptide fragments can still be paired. The two molecular species of a differentially labeled polypeptide or fragment are referred to herein as heavy and light polypeptides or fragment species. For example, a methanol heavy and light label can be $CD_3OH$ and $CH_3OH$, respectively, where D represents the isotope deuterium. Corresponding differentially labeled polypeptide species having, for example, a single label attached, would differ by three atomic mass units, which corresponds to the mass difference between $D_3$ and $H_3$ in the heavy and light labels, respectively. A differentially labeled polypeptide can be, for example, labeled and unlabeled species or alternatively, heavy labeled and light labeled species. Accordingly, the difference between the polypeptide species is attributed to a mass difference in the label attached to either or both of the heavy or light reference species.

Polypeptides can be differentially labeled by a variety of methods well known to those skilled in the art, for example, a label can be included at any position within a polypeptide for which specific chemistries or biochemical methods are available. Such positions include, for example, carboxyl and amino terminal, and amino acid side chains. A specific example of labeling carboxyl moieties, including the carboxyl terminus of a polypeptide and side chains is the esterification using methanol. Additionally cysteine can be used to attach labels through, for example, an iodoacetamide reactive group.

Polypeptides in a sample can also be labeled with a moiety having a stable isotope. For example, two different polypeptide samples can be separately labeled with moieties that are isotopically distinct, and such differentially labeled samples can be compared. A moiety can be produced that is enriched or depleted in a particular stable isotope, for example, a stable isotope of an element can contain trace amounts of a different atomic weight isotope of that element which can be depleted before incorporating into the labeling moiety. Isotopic labels that can be used to label amino acids include, for example, isotopically heavy and light versions of hydrogen, carbon, oxygen, nitrogen, sulfur and selenium. The corresponding heavy isotopes of these light atoms include: $^2H$, $^{13}C$, $^{17}O$, $^{18}O$, $^{15}N$, $^{33}S$, $^{34}S$, $^{35}S$.

Polypeptides can also be differentially labeled by labeling one polypeptide in a sample by any method and leaving the other polypeptide unlabeled. In addition, a polypeptide can be differentially labeled by labeling one polypeptide using one method, such as attachment of an ICAT™ reagent to a cysteine residue, and labeling another polypeptide using a different method, such as incorporation of an isotopically unique element so long as the two labeled polypeptides have a different mass.

As used herein, the term "paired signal" is intended to mean two mass spectra signals derived from the same polypeptide fragment that has been differentially labeled. One signal within the pair corresponds to the heavy mass labeled species, whereas the other signal corresponds to the light mass labeled species. These two signals can be distinguished from each other based on a difference in the masses of the labels that are incorporated into the polypeptide fragments. The polypeptide fragments can have one or more labels incorporated. Therefore, a difference in mass of the two signals within a pair can be equal to the difference in mass of the different labels, or any multiple thereof. A signal on a mass spectrum is also referred to as a mass spectrum peak since the signal can represent a range of charged mass values. A paired signal can be obtained from the same or different mass spectra depending on, for example, the differentially labeled polypeptide or polypeptides that are analyzed together or separately. Similarly a paired signal also can be represented on the same or different mass spectra by, for example, electronically or graphically combining or separating the individual signals corresponding to one or more paired signals.

As used herein, the term "weighting characteristic" is intended to mean a value indicator or hierarchial structure that increases the accuracy of a description or prediction of an experimental outcome or the relative importance between signal comparisons. Therefore, a weighting characteristic functions to increase the likelihood of identifying and distinguishing specific signals due to polypeptide mass from background noise or non-polypeptide signals. A weighting characteristic is evaluated together with or included in a mass signal and as such, serves as an additional factor in identifying specific mass signal over non-specific background. A weighting characteristic can be, for example, a property that correlates with an observed signal. A specific example of such a weighting characteristic is an intensity value of a mass signal. Alternatively, a weighting characteristic can be any assigned factor.

A weighting characteristic that "combines properties" or "combining properties" of mass spectrum signals as the term is used herein, is intended to mean that weighting characteristics correlating with one or more properties of each signal are either merged or consolidated or maintained separately but applied together as a value or indicator or hierarchial structure, for use in increasing the accuracy of a description or prediction of an outcome or selection. Combining properties into a single or consolidated weighting characteristic further increases the accuracy of distinguishing specific mass signals from non-specific signals in proportion to the number of properties combined into a weighting characteristic. A variety of methods, well known to those skilled in the art, can be employed to combine properties into weighting characteristics and can depend, for example, on the type of properties to be combined. For example, numbered values can be added, subtracted, multiplied, or divided. Indicators can, for example be symbolically or graphically combined. Further, hierarchial structures can be combined, for example, into data structures, spacial or graphical arrangements. Moreover, combinations of types of properties and representations also can be included in a weighting characteristic having combined properties of two or more signals. A specific example of combining properties into a weighting characteristic is where two intensity values representing two separate mass spectra peaks are multiplied to obtain a single value.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the $\epsilon$-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997), the entire book of which is incorporated herein by reference. Yet other examples include amino acids whose amide portion and, therefore, the amide backbone of the resulting peptide, has been replaced, for example, by a sugar ring, steroid, benzodiazepine or carbo cycle. See, for instance, *Burger's Medicinal Chemistry and Drug Discovery*, Ed. Manfred E. Wolff, Ch. 15, pp. 619–620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference).

As used herein, the term "satisfying amino acid" is intended to mean an amino acid having a mass that matches a mass measurement of an amino acid or that matches the difference in mass of two mass signals corresponding to a polypeptide and a fragment thereof that differs in size by a single amino acid. Similarly, satisfying amino acids refer to two or more amino acids having a combined mass that matches a mass measurement of a polypeptide or that matches the difference in mass of two mass signals corresponding to a polypeptide and a fragment thereof. Therefore, a satisfying amino acid or amino acids have a mass that fulfills an obtained or empirically determined mass of an amino acid or polypeptide molecule.

As used herein, the term "low resolution" when referring to a mass spectrum is intended to mean that the mass determination is accurate at about twenty-five parts per million (ppm) or greater of component ion fragments. A mass spectrometer that provides an accuracy of less than about 25 ppm is considered to provide high resolution spectra.

Determination of mass at lower accuracy allows the use of less expensive MS instruments which are more widely available than FT-ICR-MS. The mass determinations can be determined at an accuracy in ppm. For example the following range of mass accuracy at 1000 Da can be considered low mass accuracy: about 25 part per million (ppm) or greater than 25 ppm, and can be determined at an accuracy in ppm of about 50 ppm, or greater, of about 100 ppm or greater, about 200 ppm or greater, about 500 ppm or greater, or even about 1000 ppm or greater, sequentially each of which requires less accuracy of the MS instrument. The accuracy of the MS measurement for a particular application can be readily determined by one skilled in the art, for example, depending on the complexity of the sample to be used. The term is also intended to include low quality mass spectrometry data, which is related to resolution and accuracy, but is a measurement of the number of data pointing across a mass to change range. The lower the density of data points, the lower the quality of the information.

The invention provides a method of identifying a mass of a polypeptide fragment. The method consists of (a) obtaining a mass spectra of two differentially labeled polypeptide fragments,(b) assigning a mass and a weighting characteristic to a paired signal, and (c) selecting a paired signal distinguishable from non-peptide signals where the assigned mass indicates the mass of a polypeptide fragment within the spectrum.

The invention further provides a method for determining an amino acid sequence of a parent polypeptide. The method includes the steps of (a) obtaining mass spectra of two or more differentially labeled polypeptide fragments of a parent polypeptide; (b) assigning a mass and a weighting characteristic to two or more paired signals having a difference in mass corresponding to an integer value of the differential label, (c) selecting a paired signal from the mass spectra having an assigned mass and a weighting characteristic distinguishable from non-polypeptide signals, (d) determining the difference in mass of the polypeptide fragments, (e) assigning the mass differences a satisfying amino acid name, and (f) orienting the assigned amino acid names.

Mass determination of differentially labeled polypeptide fragments can be determined using a variety of mass spectrometry (MS) methods well known in the art. Additionally, mass spectrometry data can also be obtained, for example, from databases and utilized in the methods of the invention for determining an amino acid sequence by querying a sequence database.

A variety of mass spectrometry systems can be employed in the methods of the invention for identifying the mass of a polypeptide. Mass analyzers with high mass accuracy, high sensitivity and high resolution include, for example, matrix-assisted laser desorption time-of-flight (MALDI-TOF) mass spectrometers, ESI-TOF mass spectrometers and Fourier transform ion cyclotron mass analyzers (FT-ICR-MS) and tandem mass spectrometers (MS/MS). Other modes of MS include an electrospray ionization (ESI) process with MS and ion trap. In ion trap MS, fragments are ionized by electrospray or MALDI and then put into an ion trap. Trapped ions can then be separately analyzed by MS upon selective release from the ion trap. Fragments can also be generated in the ion trap and analyzed. It is understood that any MS methods and any combination of MS methods can be used so long as the mass of polypeptide fragments is determined.

The methods of the invention can also include a polypeptide separation step followed by a mass analysis step. Polypeptide separation and mass analysis steps can be performed independently or can be coupled in an "on line" analysis method. Various modes of polypeptide separation techniques can be coupled to a mass analyzer. For example, polypeptides can be separated by chromatography using microcapillary HPLC, by solid phase extraction-capillary electrophoresis systems that can be coupled to a mass analyzer, or by gel electrophoresis methods. A specific example of a coupled polypeptide separation and mass analysis method is micro-capillary HPLC coupled to an ESI-MS/MS system that is applied with dynamic exclusion on an ion trap MS.

The methods of the invention can utilize MS of any accuracy level and are advantageous in that MS of lower accuracy, that is higher part per million (ppm) resolution, can be routinely used without the need for more expensive instrumentation required for higher accuracy determinations. Similarly, special separation or preparation steps, also are not required for amino acid sequence determination of a polypeptide. For applications that involve high throughput analysis of a population of polypeptides, a lower accuracy mass determination can be sufficient. Lower accuracy mass determinations generally provide higher sample throughput because less time is required to make a mass determination.

The mass determinations can be determined at an accuracy, in ppm, of 1 part per million or greater than 1 ppm, and can be determined at an accuracy, in ppm, of 2.5 ppm or greater, of about 5 ppm or greater, about 10 ppm or greater, about 50 ppm or greater, about 100 ppm or greater, about 200 ppm or greater, about 500 ppm or greater, or even about 1000 ppm or greater, sequentially each of which requires less accuracy of the MS instrument. The accuracy of the MS measurement for a particular application can be readily determined by one skilled in the art, for example, depending on the complexity of the sample to be used. The adaptation of any mass spectrometer to a high throughput format, such as 96-well plate or 384 spot plate format, or to an autoinjection system that allows unattended operation, is advantageous for increasing sample throughput.

In the methods of the invention, the mass of a polypeptide or fragment thereof can be determined in the presence or absence of ion selection for producing fragment ions. Polypeptides can be additionally fractionated, for example, using polyacrylamide gel electrophoresis, and the polypeptides, also called parent polypeptides, can further be broken down into polypeptide fragments. The fragments can be additionally further fractionated by chromatography. A chromatographic fraction is subjected to mass spectrometry. Using tandem mass spectrometry (MS/MS) an ion or dominant ions can be selected in a collision cell for collision-induced dissociation (CID). Selection of a single ion can occur in a first chamber called quadrapole 1 of a mass spectrometer. An ion is selected and then fragmented in a later chamber, quadrapole 3, of a mass spectrometer. In the absence of ion selection, instead of a single ion being selected, no selection of ions is applied but, rather, all of the ions are fragmented, leading to many peptide fragments. The peptide fragments are deconvoluted to determine which correspond to a particular parent polypeptide, and such information on the mass of a fragment of a polypeptide is a characteristic associated with the polypeptide.

Determining the mass of a polypeptide or polypeptide fragment in the absence of ion selection allows for simultaneous determination of the mass of a subset of parent polypeptides from a population of polypeptides and the mass of polypeptide fragments of the subset of parent polypeptides. The simultaneous determination of masses of a subset of parent polypeptides refers to the acquisition of a subset of parent polypeptide mass values from a single sample containing a polypeptide population. The term "simultaneous" is intended to mean that the masses of parent polypeptides and polypeptide fragments are determined concurrently such that the MS method used can acquire masses of parent polypeptides and corresponding fragments in a time frame sufficient that parent and fragment masses can be correlated to the same subset of polypeptides. For example, the polypeptides being sampled in a MS method will change over time as different subsets of polypeptides elute from a chromatographic column as dictated by the flow rate of the column. A simultaneous determination occurs during a time period before a particular subset of polypeptides is altered due to the introduction of an additional polypeptide or loss of a polypeptide of the polypeptide subset that occurs as a result of on-line sampling methods.

Simultaneous determination of the mass of a subset of polypeptides can be performed, for example, in the absence of selection of a single ion for mass determination. For example, several polypeptides can be selected rather than a single ion (Masselon et al., *Anal. Chem.* 72:1918–1924 (2000), which is incorporated herein by reference). In methods of the invention, preferably greater than 5 ions, for example, 6 ions, 7 ions, 8 ions, 9 ions, 10 ions, or even greater numbers of ions are selected. Alternatively, simultaneous determination of masses of a subset of polypeptides can be performed in the absence of single ion selection or in the absence of ion selection in a source region. In such a case, the fragment ions obtained are deconvoluted to determine which ions are associated with a particular parent polypeptide and therefore useful as a characteristic associated with the parent polypeptide. Such a method can be useful for detecting and identifying less abundant ions that are not selected for fragmentation in standard MS methods.

A polypeptide or polypeptide mixture to be used in the methods of the invention can be obtained from a variety of sources such as a cell, tissue, organ or organism. A variety of methods are known in the art for cell lysis and sample preparation. Briefly, cells can be lysed, for example, by denaturants, one or more cycles of freezing and thawing, and sonication. Following lysis, the polypeptide mixture can be subjected to a fractionation to remove, for example, nucleic acid or lipid, or to remove intact subcellular fractions or organelles. Methods of lysing and fractionating cells are well known to those skilled in the art (see Scopes, *Protein Purification: Principals and Practice*, 3$^{rd}$ ed., Springer Verlag, New York (1993), the entire book of which is incorporated herein by reference).

For identification of a polypeptide, a sample or specimen can be contained in a buffer suitable for maintaining polypeptide solubility. Such buffers can include, for example, a buffer containing a detergent, including denaturants such as sodium dodecyl sulfate (SDS). Denaturants useful for solubilizing polypeptides include, for example, guanidine-HCl, guanidine-isothiocyanate and urea. In the case of guanidine-isothiocyanate, as with treatment with any reagent that can covalently modify a polypeptide, such reagents can be used so long as the change in mass due to the chemical modification is consistent, or can be differentiated, between the heavy and light labeled polypeptides. Other denaturants well known in the art can be similarly used for solubilizing polypeptides. Similarly, reducing agents such as dithiothreitol (DTT), dithioerythritol (DTE), or mercaptoethanol can be included.

The methods of the invention can additionally involve protein fractionation steps. Protein fractionation refers to any method useful for removing one or more polypeptides from a polypeptide population. Fractionation can include, for example, a centrifugation step that separates soluble from insoluble components, a method of electrophoresis, and a method of chromatography, or any combinations of such fractionation methods. For chromatographic separation, a wide variety of chromatographic media well known in the art can be used to separate polypeptide populations. For example, polypeptides can be separated based on size, charge, hydrophobicity, binding to particular dyes and other moieties associated with chromatographic media. Size exclusion, gel filtration and gel permeation resins are useful for polypeptide separation based on size. Examples of chromatographic media for charge-based separation are strong and weak anion exchange and strong and weak cation exchange resins. Hydrophobic or reverse phase chromatography can also be used.

Affinity chromatography can also be used including, for example, dye-binding resins such as Cibacron blue, substrate analogs, including analogs of cofactors such as ATP, NAD, and the like, ligands, specific antibodies, either polyclonal or monoclonal, and the like. An exemplary affinity resin includes affinity resins that bind to specific moieties that can be incorporated into a polypeptide such as an avidin resin that binds to a biotin tag on a polypeptide, as disclosed herein. The resolution and capacity of particular chromatographic media are known in the art and can be determined by those skilled in the art. The usefulness of a particular chromatographic separation for a particular application can similarly be assessed by those skilled in the art. Highly purified polypeptide samples containing only one species of polypeptide can also be used by the methods of the invention.

Those skilled in the art will be able to determine the appropriate chromatography conditions for a particular sample size or composition and will know how to obtain reproducible results for chromatographic separations under defined buffer, column dimension, and flow rate conditions. All protein fractionation methods can additionally include the use of an internal standard for assessing the reproducibility of a particular chromatographic application. Appropriate internal standards will vary depending on the chromatographic medium. Those skilled in the art will be able to determine an internal standard applicable to a method of chromatography.

Polypeptides can be fragmented by a number of methods including polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation (CID). Furthermore, a fragment can also result from multiple cleavage events such that a truncated polypeptide resulting from one cleavage event can be further truncated by additional cleavage events. Several identical or different fragments can be obtained from the original, or parent, polypeptide. The methods of the invention can use one or more polypeptide fragments from a population of polypeptide fragments.

Mass spectrometry technology exists by which several thousands of protein species can be separated, detected and quantified in a single operation. New chromatography based methods for the identification of the proteins contained in complex mixtures without the need for separation of the mixture into individual protein components are available. An example is the digestion of unseparated proteins and the analysis of the resulting complex peptide mixture by LC-MS/MS. Currently, up to 10,000 sequencing runs can be recorded in a single LC-MS analysis of 60 minutes duration. Often the duty cycle of the mass spectrometer is the rate limiting step, however, as mass spectrometers continue to improve, the number of polypeptides that can be sequenced in one run will continue to increase. Further automation and on-line analysis will greatly improve the efficiency of mass spectrometry. Therefore, as the instrumentation increases in efficiency the rate of polypeptides that can be sequenced with the methods of the invention will also concurrently increase.

The methods of the invention utilize polypeptide fragments that have been differentially labeled such that a difference in mass is detectable between the polypeptide fragments. Differential labeling of polypeptides provides a way to identify mass spectra signals that are derived from the same polypeptide fragment because the only difference between a differentially labeled polypeptide is the mass difference between heavy and light labels. Therefore, the polypeptide fragment signal can be uniquely identified as a doublet having a mass difference corresponding to the difference in mass between the labels.

Differentially labeled polypeptides are useful for determining the relative abundance of a polypeptide, or polypeptides, in two different samples. Changes in abundance of a particular polypeptide between two samples can indicate a role for that polypeptide in a biological process. For example, polypeptides from one sample can be labeled with a light isotope containing label while polypeptides from another sample are labeled with a heavy isotope containing label. The two different samples can be, for example, polypeptides extracted from a normal cell and a cancerous cell. A particular polypeptide species that is present in both samples will be chemically the same in the two samples except for the mass of the label or the chemistry used to attach the label. Because the differentially labeled polypeptides behave physicochemically the same, the same polypeptides in the two samples will ionize or fragment similarly, but still be distinguishable by MS due to the isotopic difference in the differential label. Accordingly, the relative amounts of the same polypeptides can be readily compared and quantitated.

De novo sequencing can be performed from a complex mixture of polypeptides, for example, polypeptides extracted from a sample or from different samples. De novo sequencing also can be performed on an isolated polypeptide species that has been split into two samples and labeled with light mass and heavy mass labels respectively. At least two molecules of the isolated polypeptide are needed since one molecule will be labeled with a light label and one with a heavy label. A complex mixture of polypeptides, also can be split into two samples as described above. Briefly, one sample can be labeled with a light label and one sample with a heavy label. A complex mixture of polypeptides can also be derived from two different samples where one sample is labeled with a light label and one sample is labeled with a heavy label as described in Example II. For de novo sequencing, the light and heavy labeled polypeptide samples can be separately analyzed by mass spectrometry and then compared, or the light and heavy labeled polypeptides can be mixed together before being analyzed by mass spectrometry.

When analyzed for de novo sequence generation, polypeptides that are differentially labeled provide a number of advantages. A differential label is useful because it allows one to distinguish polypeptide signals from chemical noise by virtue of the predetermined mass differential between the labels. The double signal that results from the differential labels allows easier identification and greater confidence in selecting mass spectra signals that are generated from the same polypeptide fragment. Although mass spectrometry data from any instrument can be used in the methods of the invention this increased confidence in selecting mass spectra signals further allows mass spectrometry data of lower resolution to be routinely utilized.

Differential labeling can be performed using a variety of methods known in the art, several of which are described below. One skilled in the art can readily determine appropriate variations of these methods useful for differentially labeling polypeptides.

An isotope distribution encoded tag (IDEnT)is one method of differentially labeling polypeptides. An IDEnT can be created by combining two polypeptides or pools of polypeptides that were independently subjected to derivatization using chemically identical but isotopically different reagents. Incorporation of an isotope such as chlorine that provides a unique isotopic signature also can be employed (Goodlett et al. *Anal. Chem.* 72:1112 (2000), which is incorporated herein by reference).

Another type of IDEnT is referred to as isotope-coded affinity tag (ICAT™) (Gygi et al., *Nature Biotechnol.* 17:994–999 (1999), which is incorporated herein by reference). The ICAT™ type reagent uses an affinity tag that can be differentially labeled with an isotope that is readily distinguished using mass spectrometry. For example, hydrogen and deuterium can be used as differential labels. The ICAT™ type affinity reagent consists of three elements, an affinity tag, a linker and a reactive group.

Differential labels can include various different types of reactive groups that can be covalently coupled to a polypeptide in a sample. Methods and chemistries for modifying amino acid side chains in polypeptides are well known to those skilled in the art (see, for example, Glazer et al., *Laboratory Techniques in Biochemistry and Molecular Biology: Chemical Modification of Proteins*, Chapter 3, pp. 68–120, Elsevier Biomedical Press, New York (1975), which is incorporated herein by reference; and Pierce Catalog (1994), Pierce, Rockford Ill.). Any of a variety of reactive groups can be used to incorporate a mass label so long as the reactive group can be covalently coupled to a polypeptide. For example, a reactive group can react with carboxyl groups found in Asp or Glu, or the reactive group can react with other amino acids such as His, Tyr, Arg, and Met. A reactive group can also react with amines such as Lys, for example, imidoesters and N-hydroxysuccinimidyl esters. In addition, a reactive group can also react with oxygen or sulfur using chemistry well known in the art. A reactive group can also react with a phosphate group for selective labeling of phosphopeptides, or with other covalently modified peptides, including glycopeptides, lipopeptides, or any of the covalent polypeptide modifications disclosed herein. Additionally, one skilled in the art will know or can readily determine conditions for modifying polypeptides using known reagents, incubation conditions and time of incubation to obtain conditions optimal for modification of polypeptides for use in methods of the invention.

Differential labels also can include an affinity tag that allows isolation of polypeptides coupled to the affinity reagent by binding to a cognate binding partner of the affinity tag. For polypeptide tagging, a polypeptide or polypeptides in a sample can be denatured, optionally reduced, and a chemically reactive group of the polypeptide is covalently derivatized with a chemical modification reagent. Tagged polypeptides can be easily isolated from untagged polypeptides and other components within a sample, which reduces the complexity of the sample that is to be analyzed by mass spectrometry. A specific example of an affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the labeling reagent. An affinity tag can also be used to isolate a tagged polypeptide with magnetic beads or other magnetic format suitable to isolate a magnetic affinity tag. Additionally, an affinity tagged polypeptide can be covalently trapped to bind the tagged polypeptide to a solid support, if desired.

Differential labels also can contain linkers to serve any of a variety of functions including, for example, separating constituent moieties within the mass label. For example, linkers can be useful, can be useful to separate an affinity tag from a polypeptide to reduce any interference between the tag and the polypeptide structure. Such separation can ensure predictable activities of the separated functional groups. The linker additionally can function as a site for stable isotope incorporation. Stable isotopes can be incorporated at one or more atom positions depending on the design and other functional requirements of linker. A particularly useful stable isotope pair is hydrogen and deuterium, which can be readily distinguished using mass spectrometry as light and heavy forms, respectively. Any of a number of other isotopic atoms can be incorporated into the linker so long as the heavy and light forms can be distinguished using mass spectrometry. Exemplary linkers include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999).

A variety of different differential mass labels can be used to differentially isotopically label a polypeptide or polypeptides contained in two different samples or the same sample separately labeled with light and heavy labels. For example, two chemically identical mass labels containing different isotopes can be used to covalently modify two polypeptide samples and the differentially isotopically labeled polypeptide samples can be compared for quantitative or other analysis. For example, methylation of polypeptides via esterification with methanol containing d0(no deuterium) versus d3 (three deuteriums) can be used to differentially isotopically label two polypeptide samples. Similarly, any methods well known in the art for modifying side chain amino acids in polypeptides also can be used with differentially labeled isotopes such as deuterium for hydrogen, $C^{13}$ for $C^{12}$, $O^{18}$ for $O^{16}$ (see, for example, Glazer et al., supra, 1975; Pierce Catalog, supra 1994).

Any number of isotopes can be incorporated into a polypeptide so long as differently labeled polypeptides contain a sufficient mass distinction to be detected by mass spectrometry. In addition to differentially labeling polypeptide samples by chemical modification, as described above, two polypeptide samples can be differentially labeled by digestion with a protease such as trypsin or the like in the presence of isotopically labeled substrates or reactants, for example, $O^{16}$- or $O^{18}$-labeled $H_2O$. Because the protease cleavage reaction results in the addition of water to the cleaved peptides, cleavage in the presence of differentially isotopically labeled $H_2O$ can be used to incorporate differential labels into separate polypeptide samples. It is understood that any method useful for incorporating an isotopic label to differentially label two polypeptide samples can be used in methods of the invention, so long as the samples to be compared are treated in a chemically similar fashion. Therefore, the resulting labeled polypeptides essentially will differ only by the differential label.

Isotopic labels for amino acids include heavy and light isotopic versions of the constituent elements making up amino acids. Such constituent elements include, for example, carbon, oxygen, hydrogen, nitrogen, and sulfur. In addition, other elements that are chemically or functionally similar can be substituted for the above naturally occurring elements. For example, selenium can be used as a substitute for sulfur.

Any number of isotopes can be incorporated into polypeptides so long as there is a sufficient difference in mass to be distinguished by mass spectrometry, as disclosed herein. Because the polypeptides are chemically identical except for the isotopic difference, the molecules behave in a similar physicochemical manner. Furthermore, if desired, more than two samples can be compared if a sufficient number of different isotopic labels are available such that the multiple samples can be compared and distinguished by mass spectrometry. For example, the isotopic labels d0, d4, d8, d12 can be used to label multiple samples.

Still another method to differntially label a polypeptide or polypeptides within a sample is to incubate the polypeptide sample under conditions that allow metabolic incorporation of heavy and light isotopes into two different samples for comparison by incubating a sample in the presence of an isotope. Alternatively the polypeptide samples can be incubated in media that results in depletion of a naturally occurring isotope (see, for example, Oda et al., *Proc. Natl. Acad. Sci. USA* 96:6591–6596 (1999), which is incorporated herein by reference). Such a method can be useful for a sample that is conveniently cultured, for example, a microbial sample or a primary culture of cells obtained from an individual. Polypeptides can also be labeled by in vitro methods such as labeling of polypeptide fragments from a tissue sample. Accordingly, both in vitro and in vivo methods can be used to differentially isotopically label two samples for either quantification or for the de novo sequencing methods of the invention.

Differential labeling of polypeptides at either the amino- or caroxyl-terminus is advantageous for de novo sequencing methods because the label serves as a reference point and allows the orientation of the polypeptide sequence to be determined. For example, a label that is specific for a carboxylic acid will label the carboxyl-terminus. In addition, since the amino acid residues glutamic acid and aspartic acid also contain carboxylic acid, they will also be labeled. Therefore, a carboxylic acid specific label can be used to determine partial amino acid composition, quantify relative abundance of proteins between samples, or generate de novo sequence. Additionally any combination of the above three uses also can be applied in the methods of the invention to simultaneously or sequentially obtain the resulting composition, quantification or sequence information.

Differential labeling of polypeptides also can be accomplished using differential isotopic esterification of carboxylate groups in polypeptides such as are present on the side chains of aspartic acid, glutamic acid and the carboxyl terminus. In this specific example, polypeptides are esterified using either d0- or d3-methanol which converts carboxylic acids to corresponding methyl esters. Briefly, lyophilized polypeptides are methylated after solubilization in a solution of methanolic HCl as described in Example 1. This carboxylic acid-specific label can be used to determine partial amino acid composition, quantify relative abundance of proteins between samples or generate de novo sequence. Additionaly, any combination of the above three uses also can be applied in the methods of the invention to simultaneously or sequentially obtain the resulting composition, quantification or sequence information.

Differential labeling of a polypeptide or polypeptides also can be accomplished by a variety of other methods well known in the art. For example, a polypeptide fragment can be differentially labeled by having one sample of the fragment labeled and one sample of the fragment unlabeled because the two fragments will differ by a determined mass. Further, a fragment can be differentially labeled using two or more different types of mass labels. ICAT™ type label can be used together with methyl-esterification so long as a difference in mass results from the differentially labeled samples.

The choice of location of a differential label can supply additional information useful for determining an amino acid sequence de novo. For example, if a differential label is specific for one terminus of a polypeptide, determination of the directionality of the amino acid sequence can be accomplished with less computational effort. Also, by attaching a differential label to a specific amino acid, for example a cysteine residue, the label can additionally provide partial amino acid composition information about the polypeptide.

A polypeptide can be labeled at any residue within the amino acid chain including the carboxyl or amino terminus, or an internal site. In addition, a polypeptide can be labeled at any combination of a terminal and an internal site. For example, the methyl-esterification method labels carboxylic acids present at the carboxyl terminus of each polypeptide and also present in two amino acids, aspartic acid and glutamic acid. Therefore, depending on the sequence of the polypeptide, a terminal label and possibly one or more internal labels will be present. A polypeptide can be labeled only at internal amino acid residues by using, for example, an ICAT™ reagent. This reagent specifically labels cysteine residues. A polypeptide can be labeled only at one terminus, for example at the carboxyl terminus, by digesting a polypeptide with trypsin in the presence of isotopically labeled water. In addition, combinations of labeling methods can be used to label different combinations of termini or internal residues. For example, a polypeptide can be labeled using an ICAT™ reagent and isotopically labeled methanol resulting in the labeling of the carboxyl terminus and glutamic acids, aspartic acids, and cysteines within the polypeptide.

The invention can utilize labeling methods that label all of the polypeptides in a mixture, regardless of amino acid composition, or methods that label only a subset of polypeptides in a mixture. Methods like ICAT™ type tagging will only label polypeptides that contain a cysteine residue. In the case of yeast proteome analysis, it is predicted that 92% of all ORFs will be labeled. In contrast, since esterification labels the carboxyl terminus of any polypeptide, all polypeptides in a sample should be labeled.

Figure 2:
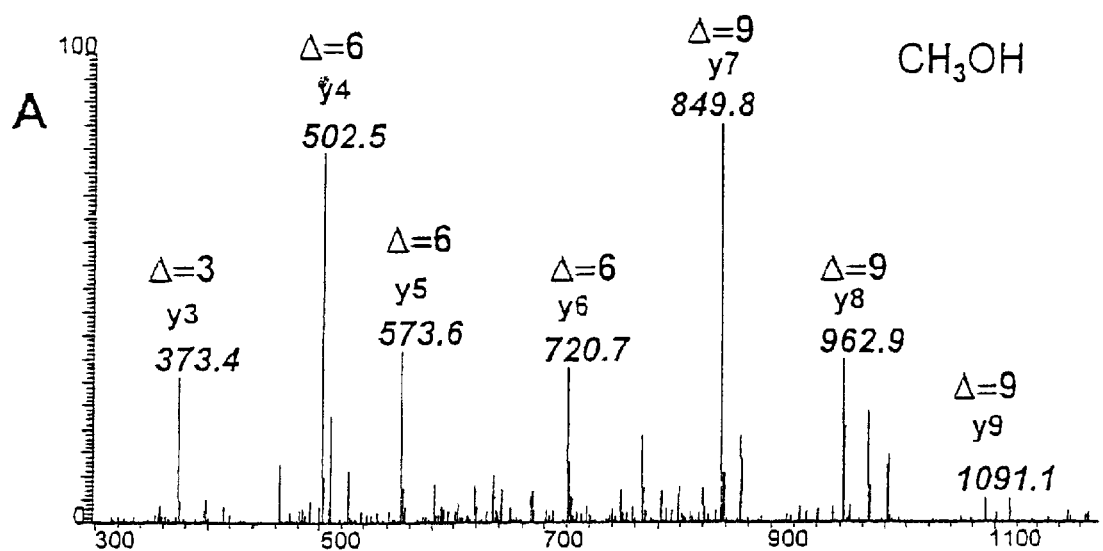
FIG. 2 shows tandem mass spectra for d0- (A) and d3-methyl (B) esters of a polypeptide from human protein GB01.
Figure 2:
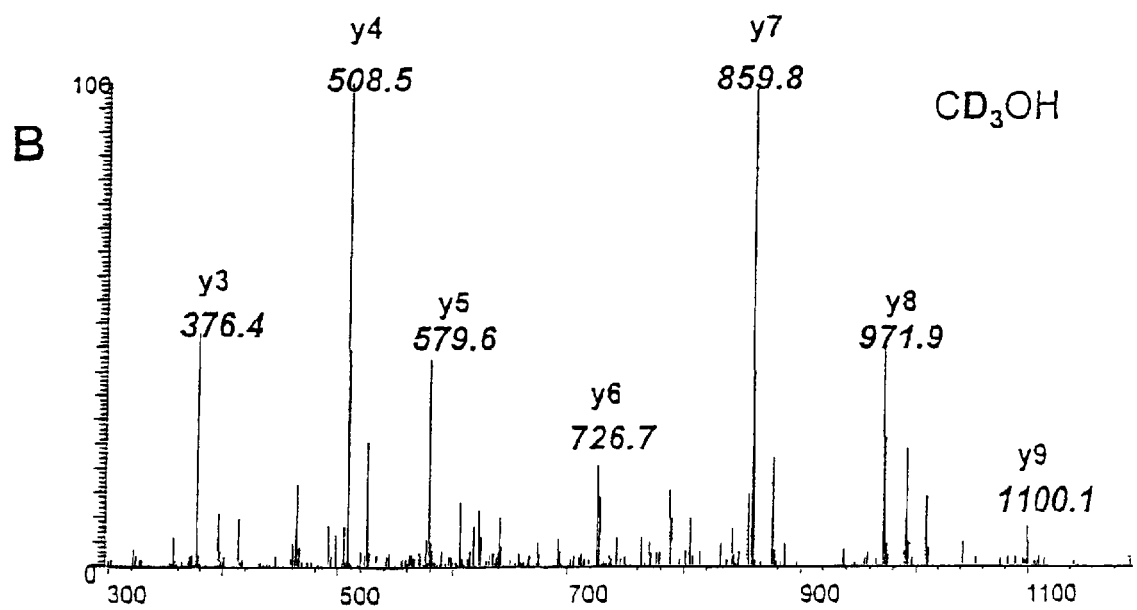

Mass analysis of polypeptides from a mass spectrometer is represented by a graph of mass peaks where the y axis is the relative abundance of a polypeptide fragment and the x axis is the mass of the polypeptide fragment (m) divided by the charge (z) of the polypeptide fragment. Mass peaks are often displayed as individual lines or signals, however when an expanded view of an area of the mass spectra is investigated the signal is actually a peak with a distribution of masses. When a polypeptide or a mixture of polypeptides are differentially labeled, the heavy and light labeled samples can be displayed, for example, on an individual graph as shown in FIG. 2 or the combined spectra can be displayed on a single graph as shown in FIG. 1.

A mass spectra of differentially labeled polypeptides contains paired signals which are signals derived from the same polypeptide fragment species that has been differentially labeled. These two signals can be distinguished from each other based on a difference in mass of the labels that are incorporated into the polypeptide fragments. The polypeptide fragments can have one or more labels incorporated. Therefore, the difference in mass of the two signals can be equal to the difference in mass of the different labels or any multiple thereof. Hence if the difference in mass between the two signals is 3 atomic mass units (AMU), then mass differentials of 3, 6, 9, 12, and other multiples of 3 could be observed.

The difference in mass between the differential label is represented above as an integer. However, those skilled in the art will understand that the observed value might not be an exact integer value because of insignificant experimental measurement error. For example, the mass difference of the labels when using the isotopic d0- and d3-methyl esters as light and heavy labels respectively, is the integer value 3. However, one skilled in the art would be able to determine if two differentially labeled signals were derived from the same polypeptide fragment if the observed mass difference was measured to be slightly lower or slightly higher than about 3. A value within a 7.5–20% range of the differential mass value, but more generally a 10–15% range, is acceptable. Therefore, if a mass difference was measure to be, for example, between about 2.77 and 3.6 AMU, or 2.7 and 3.45 AMU, one of skill in the art would know or could readily determine, that the signals were derived from the same polypeptide fragment species that had been differentially labeled.

Because paired signals can be identified based on the difference in mass of the differential labels employed, it is possible to distinguish paired signals from non-polypeptide related signals. These non-polypeptide related signals correspond to background noise and are due to, for example, non-polypeptide chemical polymers, clusters of ions, non-covalents of $CH_3CN$, $CH_3CO_2H$, and electronic noise from the instrument. Moreover, because of the increased confidence that the paired signals chosen represent the true mass of a polypeptide fragment, the methods of the invention can advantageously utilize low resolution mass spectra data for de novo sequencing. For example, correct signals can be chosen from low resolution data, from among the many non-polypeptide peaks, because paired peaks corresponding to authentic polypeptide signals, can be identified based on their correlation with a predetermined mass differential of heavy and light labels. This difference in mass can be used in the de novo sequencing methods of the invention.

In the de novo sequencing methods of the invention, amino acid sequence of a parent polypeptide is determined directly from mass spectra or from a data set derived from mass spectra. Therefore, using the de novo sequencing methods of the invention, it is unnecessary to query a polypeptide sequence database with polypeptide fragment masses in order to determine its sequence through matching with a deposited sequence. An advantage of de novo sequencing is that it eliminates ambiguities due to the identification of multiple isobars resulting from a database query.

In the de novo sequencing methods of the invention a mass can be assigned to a paired signal by recording the mass as determined by the mass spectrometer of either the light labeled fragment or the heavy labeled fragment of the paired signal. The assigned mass indicates the mass of the polypeptide fragment within the spectra. Any of several different weighting characteristics also can be given to paired signals. These weighting characteristics are properties of each signal within the paired signals and when combined serve to further distinguish polypeptide signals from non-polypeptide signals. A weighting characteristic can be based, for example, on a property that correlates with an observed signal. Similarly, a weighting characteristic also can be an inherent property or attribute of the signal. Although a weighting characteristic can be obtained from a single heavy or light signal resulting from a differentially labeled polypeptide sample, combining weighting characteristics from paired signals further increases the accuracy and reliability of identifying specific polypeptide signals. The weighting characteristic of single or combined properties can then be attached or associated with the mass of either the heavy or light polypeptide fragment signal and further used in the methods of the invention. An example of a weighting characteristic is the intensity value of either of the mass signals that make up a paired signal.

Another specific example of a weighting characteristic is the resolution value of either of the mass signals, where resolution is the ratio of the mass of a signal to the difference in mass representing the width of a signal taken at 50 percent of its height. A variety of other properties of a signal are known to those skilled in the art and also can be used as a weighting characteristic in the methods of the invention. Weighting characteristics also can be combined by any of a variety of methods well known in the art. For example, weighting characteristics can be combined by multiplication, addition, exponentiation exemption as well as higher order transformations and manipulations. Additionally, subtraction and division also can be used to combine weighting characteristics, although enhancement of signal selection is generally more optimal when the combined value increases compared to the value of either single weighting characteristic. A combined weighting characteristic empirically serves to increase confidence in selection of specific polypeptide signals and amino acid sequence determination. Alternatively, and as described further below, a combined weighting characteristic also can computationally serve to increase confidence in selection of specific polypeptide signals as well as the orientation of the linear sequence of amino acids of a parent polypeptide. Moreover, a weighting characteristic or weighting characteristics combining properties of paired signals also can be represented by any of a variety of means other than numerical values. For example, weighting characteristics can be symbols, such as a plus or minus sign, or arrows. Weighting characteristics also can be represented by different shades or colors. Numerous other means are similarly applicable for representing a property of a signal as a weighting characteristic and are well known to those skilled in the art.

The invention provides a method of determining an amino sequence of a parent polypeptide by obtaining, from any source, mass spectra of two or more differentially labeled polypeptide fragments of a parent polypeptide, assigning a mass and a weighting characteristic to two or more paired signals, as described above, and selecting paired signals having an assigned mass and a weighting characteristic distinguishable from non-peptide signals. In addition, the mass difference between signals can be determined and assigned a satisfying amino acid name. These amino acid names can be oriented to provide the amino acid sequence of the parent polypeptide.

In order to generate amino acid sequence of a parent polypeptide de novo, differences in mass of signals from the polypeptide fragments are determined. As described previously, polypeptide fragments of a parent polypeptide can be generated, for example, sequentially by first selecting a parent polypeptide ion and then subjecting it to fragmentation. Tandem mass spectrometry is one type of mass analysis that can routinely perform such ion selection and fragmentation steps. Alternatively, polypeptide fragments can be analyzed simultaneously with their respective parent polypeptides in either MS or MS/MS modes of analysis, for example. In this specific embodiment numerous different parent polypeptides can be sequenced simultaneously in a single mass analysis.

De novo amino acid sequence determination is performed by fragmenting one or more parent polypeptides in a mass spectrometer and identifying the masses of the resulting polypeptide fragments. Either by ionization methods or by CID, a parent polypeptide will be fragmented at several to many different locations along the polypeptide backbone. Such fragmentation will result in a range of different size polypeptide fragments corresponding to the parent polypeptide. Differences in mass between the polypeptide fragments will correspond to the mass of one or more amino acids which constitute the amino acid residue or residues located at the intervening position between one polypeptide fragment and the next mass size smaller polypeptide fragment. Mass differences for polypeptide fragments representing the entire distribution spanning a parent polypeptide, or region of a parent polypeptide for which sequence is desired, are calculated and the corresponding amino acid masses are identified. The resulting determination will provide an amino acid composition of the corresponding parent polypeptide.

Where a mass difference corresponds to more than one possible amino acid, all of such different, but closely related amino acids can be assigned as a satisfying amino acid. Comparison of diffrent sites of polypeptide fragments can be used to select the satisfying amino acids within a mass related subgroup that best fits the reference mass difference. Additionally, further de novo sequencing analysis can be performed using mass labels that target a different set of amino acids, or through analysis of the alternative b- or y-ion signals, to obtain the corresponding satisfying amino acid for the reference mass difference. Amino acids which exhibit closely related masses included, for examplel Leu, Ile, Asn, and Asp, ranging between 113–115 AMU and Lys and Glu at 128 and 129 AMU, respectively.

Amino acid sequence can be determined by identifying the orientation of polypeptide fragments with respect to either the carboxyl- or amino-terminal end of the parent polypeptide. Orientation is determined by identifying the location of peptide bond cleavage with respect to either the carboxyl- or amino-terminal end. The resulting polypeptide fragments are termed "y" and "b" ions, respectively. As will be described further below, amino acid sequence of the parent polypeptide can be determined from either or both of the y- or b-ions using the de novo sequencing methods of the invention. Employing differential mass labels in the methods of the invention augments both the selection of polypeptide fragment signals over non-polypeptide signals and determination of consecutive amino acid sequence orientation to reliably yield the amino acid sequence of a parent polypeptide. Differential labeling performs these functions whether they are located at internal residues, either or both carboxyl- and amino-terminal residues, or both internal and terminal residues. It can be desirable to sequence one or more regions of the parent polypeptide using a different type of differential label to obtain an independent sequence result.

Briefly, using differentially labeled polypeptide fragments, one labeled fragment of the pair is chosen to represent the mass of the polypeptide fragment and the analysis described above is performed by compensating for the mass of the attached label or labels. For example, either the heavy or light labeled signals can be used in the analysis. Similarly, an amino acid sequence can be determined de novo using, for example, either of the observed masses because of the internal consistency of the attached mass labels, or alternatively, by using calculated masses representing the masses of the observed polypeptides without labels. Given the teachings and guidance provided herein, a variety of data transformations and manipulations also can be performed prior to, during or subsequent to performing de novo sequence analysis as described above and further below. The mass difference between the representative mass of a paired signal and the next representative mass of a paired signal is calculated and compared to known masses of amino acid residues. Additionally, masses of modified amino acid residues have also been calculated, or can be calculated, and similarly can be used in the de novo sequencing methods of the invention. The amino acid or modified amino acid mass that best corresponds to the mass difference in the two representative signals of each paired signal is assigned to that mass difference. By continuing this process sequentially through the mass spectra paired signals, an amino acid chain is generated. The orientation of this chain is determined by the position of the label.

As briefly described above, polypeptide fragment ions can be differentiated according to the amide bond that fragments, and the end of the polypeptide that retains, a charge after fragmentation. If the positive charge associated with the parent polypeptide ion remains on the amino-terminal side of the fragmented amine bond, this fragment ion is referred to as a b-ion. Conversely, a polypeptide fragment is referred to as a y-ion if the charge remains on the carboxyl-terminal side of the broken amide bond. Either the b-ions, y-ions or both can be used for amino acid sequence determination. For example, in regions of the spectra where y-ions are more clearly resoved, those y-ions can be used to generate amino acid sequence for the corresponding region of the parent polypeptide. Similarly, in regions where b-ions are more clearly resolved, those ions can be selected for determination of the corresponding amino acid sequence. Once determined, the resulting partial amino acid sequences can be combined to give the complete amino acid sequence of the parent polypeptide. Similarly, where an amino acid sequence has been determined using y-ions, for example, it can be desirable to confirm the sequence using b-ions resulting from the opposite orientation. Charge assignment of polypeptide fragment ions will be known, or can be determined by those skilled in the art. Moreover, predetermined mass labels employed together with predetermined characteristics can be used to enhance charge assignment of polypeptide fragment ions within both simple and complex spectra as well as across a wide range of mass to charge ratios (m/z).

For example, labeling of either the amino- or carboxyl-terminus of a polypeptide can be performed to assign directionality to polypeptide fragment ions resulting from mass spectra data. Briefly, where a polypeptide is differentially labeled by, for example, isotopic d0 and d3 methyl-esterification, the carboxyl-terminus of the polypeptide will be labeled. Glutamic and aspartic acid residues will similarly be labeled, if present in the polypeptide fragment. For the specific example where the polypeptide fragment does not contain any glutamic or aspartic acid residues, this reaction will increase the mass of the polypeptide fragment by the mass differential of the label which is about 3 AMU. Similarly, each glutamic or aspartic acid in the polypeptide fragment will increase the mass differential by about 3 AMU, respectively. Therefore, the mass of each signal in the y-ion series will be increased by 3 mass units compared to the corresponding signals obtained from the other d0-labeled polypeptide where there are no glutamic or aspartic acids present, and by a multiple of 3 AMU for each glutamic or aspartic present.

Similarly, attaching a differential label to an amino-terminus having a mass difference corresponding to 3 AMU, will produce a resulting b-ion series that will be increased by 3 mass units in the heavy labeled sample compared to the corresponding signals obtained from the light labeled sample. For each amino acid in the polypeptide fragment containing an amino group in its side chain, the mass differential will be corresponding increased by heavy label attachment.

Additionally, two different sets of differential labels can be used simultaneously to label both the carboxyl- and amino-terminal. For example, a differential label specific for the carboxyl-terminus having, for example, a mass difference of about 3 AMU can be used simultaneously with a differential label specific for the amino-terminus having, for example, a mass difference of about 5 AMU. In this specific example, heavy labeled y-ion series will be increased by 3 mass units while the heavy labeled b-ion series will be increased by 5 mass units compared to their respective light labeled samples. These predetermined mass differences uniquely associated with either a carboxyl- or amino-terminal label will identify y- and b-ions, respectively. Combinations of different sets of differential labels can be performed simultaneously, as described above, or separately in parallel or series format, for example.

Given the teachings and guidance provided herein, combinations of differential label sets can be employed for terminal amino acid residues, internal amino acid residues or both. Therefore, the methods of the invention can utilize a wide variety of compatible characteristics and labeling methods to attach differential labels of a single mass differential or sets of labels having different mass differentials at specific amino acids or amino acid positions within a parent polypeptide to selectively label from a few, to many, to all amino acids.

As described above, labeling of internal amino acid residues similarly increases the difference in mass between heavy and light labeled polypeptide fragments. Briefly, where an internal aspartic or glutamic acid also is present in the polypeptide, the difference in mass will be a multiple of the mass differential of the labels. In the specific example of a polypeptide fragment containing four aspartic acid residues, the difference in mass for this polypeptide fragment would be twelve mass units, or fifteen mass units when including the carboxyl-terminal label. Mass differentials due to internally labeled amino acids also can be utilized in determining amino acid sequence because their respective placement within the sequence is provided based on the mass difference between the heavy and light differentially labeled polypeptides fragments. For example, an increase in mass difference between two polypeptide fragments of a parent polypeptide that is due to internally labeled amino acids will correspond to a larger polypeptide fragment.

The invention also provides a method of determining amino acid sequence of a polypeptide. The method consists of constructing a graph from mass spectra of two or more differentially labeled polypeptides. The graph contains a node with mass m, number of labels n, intensity i, and mass differential of labels $\delta$. A node is created corresponding to a paired signal having masses of about m and about m+n$\delta$, and a labeled weighted directed edge is added to the graph between any two nodes corresponding to a mass of an amino acid. The graph can be constructed by visual representation or a digital means.

It is understood that different types of descriptions or representations including, for example, visual displays, matrices, numerical displays, or descriptions, in both digital or analog form can be utilized in the computational methods of the invention. The methods of the invention identify, assign and manipulate information corresponding to characteristic properties of paired signals. Therefore, any type of processing structure, whether electronic or visual can be employed in the methods of the inventions so long as they are able to represent characteristic properties of paired signals and perform the steps of the method as described herein. Therefore, inputs to the methods such as mass values and relationships between paired signal can be utilized as values without being transformed into, for example, a graph or other visual display. Additionally, computer programs also can be produced based on the methods of the invention that substitute any of a variety of intermediate outputs for the graphical or other representations as described below. The final output of the methods of the invention will be the amino acid sequence of one or more parent polypeptide.

The computational methods of the invention will be described with references to a graphical display or description of the intermediate output. However, and as described above, essentially any form of intermediate output or representation for illustration purposes can be similarly used instead of the spectrum graph as described below. Those skilled in the art will know or can readily determine what description or representation is applicable for a particular application or purpose. For example, spectral data from mass spectrometry can be transformed to a direct acyclic or other comparable graph, termed a spectrum graph. In this specific type of graph, a node corresponds to a mass peak, and an edge, labeled by one or more amino acids, connects two nodes differing by the total mass of the amino acids. A mass peak is transformed into several nodes in the graph, and each node represents a possible prefix subsequence (ion) for the peak. Finally, a series of computational instructions and decisions or, an algorithm is used to find a longest or highest scoring path in the graph. The concatenation of edge labels in the path gives one or multiple candidate polypeptide sequences.

The computational method described herein for de novo sequence derivation involves several inputs. First, the mass spectra of a differentially labeled polypeptide is obtained, for example, mass spectra of light and heavy differentially labeled spectra resulting from polypeptides that are modified with light and heavy versions of a label. Both spectra are associated with a total peptide mass computed by the mass spectrometer and designated as $mass_L$ and $mass_H$. In addition, the masses of unlabeled and labeled amino acids, and optionally the masses of known or suspected post-translational modifications is known and available for use in the method. As described previously, the mass difference between the differential, or light and heavy versions of the label, designated $\delta$, is also pre-determined as is the possible fragment ion series (b or y ions), which is determined by the location of the label. The mass measurement uncertainty $\epsilon$, and the minimum number of labels per fragment ion, $n_0$, are also determined.

Exemplarily, steps of the paired spectra de novo polypeptide sequencing method are as follows. First, record the total peptide mass, M, as the mass of the light label ($mass_L$). Then the total number of labels on the polypeptide, N, can be computed as ($mass_H-mass_L$)/$\delta$. The number of labels, n, and the total number of labels, N, will be integer values.

Next a correlation(n) spectrum is computed according to the following rules for each integer value of n ranging from the minimum number of labels, $n_0$ to the total number of labels, N. For each pair of peaks $P_L$ in the light spectrum and $P_H$ in the heavy spectrum with masses mass($P_L$) and mass ($P_H$) and intensities int($P_L$) and int ($P_H$), respectively, if mass ($P_H$)=mass ($P_L$)+n*$\delta$±$\epsilon$ then add a peak with mass($P_L$) and intensity int($P_H$)*int($P_L$) to correlation(n) spectrum.

The next step is to construct a graph with the following nodes and edges, using contributions from all N−$n_0$+1 correlation(n) spectra. For spectrum nodes, add a node with mass m, number of labels n, and intensity i (m,n,i) for each peak of mass m in the correlation(n) spectrum with intensity i. If both b and y ion series are possible, for each node (m,n,i), add a complement node with mass M−m, number of labels N−n+$n_0$, and intensity i, (M−m,N−n+$n_0$,i).

For the spectrum graph edges, add labeled weighted directed edges to the spectrum graph from any node 1 ($m_1,n_1,i_1$) to any node 2 ($m_2,n_2,i_2$) with weight $i_1*i_2$ and label 'aa' if one of the following is satisfied:

if($m_1-m_2$)=mass(unlabeled amino acid 'aa')±$\epsilon$ and($n_1-n_2$)=0.

if($m_1-m_2$)=mass(labeled amino acid 'aa')±$\epsilon$ and($n_1-n_2$)=1.

This method can be used to determine amino acid sequence of a polypeptide.

Additionally, the computational method described herein for de novo sequence determination from differentially labeled polypeptides can involve comparing the mass spectra of polypeptides labeled with one label against the same peptides labeled with the other label to remove noise. Also, mass spectra with a polypeptide peptide mass difference within a reasonable range, for example, corresponding to 1–5 labels per polypeptide fragment, are selected. If the polypeptide fragments were labeled with a reagent that defines one of the termini then mass spectra from the opposite fragment ion series can be removed. For example, if the polypeptide fragments were labeled with d0- and d3-methanol then the carboxyl terminus would be labeled. Any b-ion fragments (generated by amino terminal cleavage) lacking aspartic and/or glutamic acid residues are removed. In addition, the number of methyl esters located to specific y-ions (generated by carboxyl terminal cleavage), given by the integer n, adds a useful constraint for subsequent de novo sequencing. Furthermore, neighborhood filtering of peaks from both spectra can help to remove low intensity noise.

Known or suspected post-translational modifications of an amino acid in the polypeptide can be included in the method. For example, in the case of a known post-translational modification of mass mass(mod), add an edge with weight $i_1*i_2$ and label 'mod aa' if one of the following is satisfied:

if($m_1-m_2$)=mass(unlabeled amino acid 'aa')+mass(mod)±$\epsilon$ and ($n_1-n_2$)=0.

if($m_1-m_2$)=mass(labeled amino acid 'aa')+mass(mod)±$\epsilon$ and ($n_1-n_2$)=1.

The boundaries of the nodes can be utilized by creating a source node with mass M, number of labels N, and fixed intensity $I_s$, (M,N,$I_s$). Also, a terminus can be created node with mass 0, minimum number of labels $n_0$, and fixed intensity $I_t$ (0,$n_0$,$I_t$). In addition, optionally, unlabeled edges from the source node to other nodes, or from nodes to the terminus node, can be added provided reasonable constraints regarding ($m_1-m_2$) and ($n_1-N_2$) are satisfied.

A path can be computed through the spectrum graph from the source node to terminus node in which no node and its complement both appear. Furthermore, in the case of post-translational modifications, a single path can have no more than the allowed number of modifications. In order to prioritize the paths through the spectrum graph, a score can be assigned to each path. Many scoring schemes are possible, such as summing the path edge weights, summing together weights for paths with equivalent labels, and adding a bonus to paths with tryptic carboxyl termini (arginine or lysine amino acids). Path finding can be made more efficient by employing a bounded search using pre-computed longest path scores from each node to the terminus node. The output of the method is top scoring sequences as the labels of the edges along highest weight paths from the source node to the terminus node.

The method of the invention can utilize data where the number of labels, n, is equal to zero. In this case the paired spectra will be overlapping because there is no difference in mass. A weighting characteristic can still be assigned to this paired spectra and the data utilized in the methods of the invention.

An additional optional feature in the method is the inclusion of internal multiple amino acid edges to account for degenerate sequence. These edges can enable a direct jump over a missing ion edge and assign that edge a degenerate amino acid designation. For example, a de novo derived sequence, -PDNAVITIG- (SEQ ID NO: 8), from a carboxyl-terminus labeled peptide can differ from the true sequence, SYELPDGQVITIGNER, (SEQ ID NO: 7), at a di-amino acid stretch (i.e. NA vs. GQ) due to preferential cleavage at the leucinyl-proline bond that results in a missing y-9 fragment ion. A method with internal multiple amino acid edges can jump from the y-8 to the y-10 ion and the resulting sequence will have a degenerate amino acid at the y-9 position so that the resulting sequence will include the correct sequence.

The steps of the method of the invention can be repeated one or more times depending on the number of signals present in the spectra and the number of polypeptides that are to be sequenced. In addition, the steps of the method can be performed manually or in an automated fashion. For example, automation of the method can be accomplished by a computer program executed by a computer apparatus.

The mass spectrometry data used in the computational method can be obtained from any data set including data sets obtained from a database. Databases can display mass spectra data in different formats. The computational method can utilize information from databases that display mass spectra in numerical format as well as those that display the mass spectra graphically. If desired, these numbers can be transformed into graphical representations or used directly in the steps of the method. Known protein sequences in a database also can be utilized by the methods of the invention. For example, the de novo sequences of a polypeptide can be determined by comparing differences in the sequence of the polypeptide against sequences of a closely related polypeptide, for example from a different species in a database. The difference in mass between an amino acid in the sequence of the polypeptide and the mass of the corresponding amino acid the closely related protein in the database can be utilized by the methods of the invention.

If desired, mass spectrometry data can be conveniently stored on a computer readable medium. Accordingly, the invention provides a computer readable medium comprising mass spectrometry data and methods. Such a computer readable medium is useful for comparing the characteristics of a polypeptide, which can be conveniently performed on a computer apparatus. The use of a computer apparatus is convenient since comparison of characteristics and/or quantitative amounts of a polypeptide in a sample are possible. The method can be conveniently accessed using appropriate hardware, software, and/or networking, for example, using hardware interfaced with networks, including the internet.

By using various hardware, software and network combinations, the methods of the invention including the step of comparing mass spectrometry data can be conveniently performed in a variety of configurations. Accordingly, the invention additionally provides a computer apparatus for carrying out computer executable steps corresponding to steps of invention methods. For example, a single computer apparatus can contain instructions for carrying out the computer executable step(s) of the method of the invention.

Alternatively, the computer apparatus can contain instructions for carrying out the steps of an invention method while the mass spectrometry data is stored on a separate medium. Such a separate computer readable medium can be another computer apparatus, a storage medium such as a floppy disk, Zip disk or a server such as a file-server, which can be accessed by a carrier wave such as an electromagnetic carrier wave. Thus, a computer apparatus containing mass spectrometry data or a file-server on which it is stored can be remotely accessed via a network such as the internet. One skilled in the art will know or can readily determine appropriate hardware, software or network interfaces that allow interconnection of an invention computer apparatus.

The invention further provides a method of determining the amino acid sequence of a polypeptide by first performing the step of differentially labeling two or more polypeptide mixtures. The method involves using the graphing method described above.

The invention also provides a method of determining an amino acid sequence of a parent polypeptide, by obtaining mass spectra of two or more differentially labeled polypeptide fragments of a parent polypeptide where the differential label marks a terminal amino acid residue and at least one internal amino acid residue using the methods described herein.

The methods of the invention can utilize polypeptides labeled only with an internal amino acid residue, only a terminal amino acid residue, two or more labeled internal residues, labels at both termini of the polypeptide, or any combination of the above. Because the mass differential of the label is known, information is available for the method to generate de novo sequence regardless of the location of the labels. In the example of isotopic methyl-esterification where the carboxyl terminus is labeled, the carboxyl terminus will have a difference in label corresponding to the mass differential of the labels, and hence it will always have the lowest integer difference in mass and serve as a reference point. As further labels are incorporated into the polypeptide, multiples of the mass differential of labels will be present on peptide fragments in the mass spectra.

The method can additionally utilize a paired signal corresponding to a different internal residue having an integer difference in mass corresponding to the differential label, and a paired signal corresponding to two or more internal amino acid residues having the same integer difference in mass.

The methods of the invention can be applied to other macromolecules and are thus not limited to polypeptides. For example, oligonucleotides and carbohydrates can be ionized and detected by mass spectrometry and DNA sequencing can be performed by mass spectrometry. In addition, mass values or other method inputs determined by methods other than mass spectrometry can be utilized by the methods of the invention.

It is understood that modifications which do not substantially affect the activity of the various embodiments of this invention are also included within the definition of the invention provided herein. Accordingly, the following examples are intended to illustrate but not limit the present invention.

EXAMPLE I

Polypeptide Mass Quantitation Using Methyl-Esterification as a Differential Label This example shows a method for differential isotopic esterification to create a differential label specific to carboxylate groups in peptides such as are present on the side chains of aspartic acid, glutamic acid and the carboxyl terminus. This carboxylic acid-specific label is used to determine partial amino acid composition, quantify relative abundance of proteins between samples and generate de novo sequence.

As an example of how differential isotopic esterification can be used to measure the relative quantification of proteins between mixtures that are qualitatively similar, but differ in the relative abundance of individual proteins, a contrived mixture using myoglobin was prepared. Myoglobin was digested with trypsin and divided into equal aliquots that were then separately esterified using either d0- or d3-methanol.

Briefly, methyl-esterification was performed by first proteolyzing sperm whale myoglobin to peptides using trypsin. Prior to methylation polypeptide solutions were lyophilized to dryness in a Speedvac. Lyophilized peptides were methylated after solubilization in a solution of methanolic HCl. Esterification proceeded for 2 hours at room temperature and the reaction was stopped by lyophilization to dryness. Methylated peptides were solubilized in 0.1% acetic acid for LC/MS/MS analysis. The methanolic HCl solution was prepared fresh daily by slow drop-wise addition of 160 mL of acetyl chloride to 1 mL of d0- or d3-methanol with stirring on ice. After addition of acetyl chloride the reaction was stirred for 5 min. at room temperature prior to use.

The two differentially labeled samples were then combined such that the d0-methyl esterified peptides were present at twice the abundance of the d3-methyl esterified peptides. The mixture was then analyzed by micro-capillary LC/MS/MS to check the relative abundance of peptides between the two pools of myoglobin.

Briefly, mass spectrometry was performed by loading peptides onto microcapillary columns (ODSAQ 5 mm; 7 cm×50 mm) that were prepared by slurry packing with a pressure cell (Mass Evolution, Inc. Spring, Tex.) set to 1000 psi. Other details of the column preparation and use are as described elsewhere (Goodlett, supra 2000). Collision induced dissociation (CID) of peptides was carried out on an ion trap (ThermoFinnigan, San Jose, Calif.) equipped with a home built electrospray ionization source or a similar commercial source (Mass Evolution, Inc. Spring, Tex.). Peptides were introduced into the mass spectrometer by elution from the microcapillary column with a linear gradient of acetonitrile formed with a binary HPLC pump (Agilent Technologies, Wilmington, Del.). Solvent A consisted of 0.2% acetic acid and 0.005% heptafluorobutyric acid while solvent B was acetonitrile. Linear gradients were formed at a rate of 0–65% B in 30 min. Peptides were selected for CID by a data-dependent process that dynamically excluded previously fragmented ions from repeated fragmentation for 3 minutes.

An example of the results can be seen in FIG. 1 where a single m/z window in time from the total ion chromatogram is presented. As expected there are a number of ion pairs present at the expected 2:1 ratio. Notice that the Δ m/z values for each related polypeptide ion pair will be at least Δ m/z=3 for singly protonated polypeptide ions due to esterification of the carboxyl-terminus. However, the Δ m/z value for each related polypeptide ion pair can vary as the number of carboxylate-containing amino acids such as aspartic acid and glutamic acid present in the polypeptide sequence vary.

Proteins were identified from tandem mass spectra of methylated peptides using SEQUEST (Eng, et al. *J. Am. Soc. Mass Spectrom* 5:976(1994)) to search a non-redundant protein database. SEQUEST searches were conducted twice such that all carboxylic acids were first considered as modified with d0-methanol and then the analysis repeated for the d3-methyl esters. For relative quantification of proteins, the area under the curve for the ion current trace of a given charge state for the d0-methylated polypeptide was normalized to that of the same charge state for the d3-methylated polypeptide using XPRESSÔ™ software. SEQUEST scores above a correlation of 2.0 and a cross-correlation of 0.2 were considered as a minimum for identification purposes.

EXAMPLE II

Quantitation Using Complex Biological Mixtures

This example shows how quantitation can be performed using a complex biological mixture instead of a purified protein as in Example I. Lipid rafts contain about 70 protein and are thought to play an important role in T-cell signaling via the T-cell receptor (TCR). Comparison of lipid rafts isolated from T-cells treated with OKT3 to control T-cells is a good biological model of sufficient complexity to test this methodology for protein quantification. For this study lipid raft proteins were compared between those harvested from Jurkat T-cells (control) and Jurkat T-cells treated with anti-human CD3ε monoclonal antibody OKT3 a process that simulates activation of the T-cell receptor complex of proteins.

Briefly, Jurkat T cells were maintained at 37° C. and 5% $CO_2$ in a humidified incubator according to standard procedures in RPMI 1640 medium supplemented to 10% fetal bovine serum, 2 mM L-glutamine, 1 mM sodium pyruvate and 55 mM β-mercaptoethanol. For stimulation, cells were spun down and re-suspended at ~$2 \times 10^7$/ml in the above medium and cooled on ice for at least 10 min. Aliquots of cells to be stimulated had the anti-human CD3ε monoclonal antibody OKT3 added to a concentration of 2 mg/ml (from a 1 mg/ml stock). Cells were incubated on ice a further 15 min. Samples were then briefly spun down at 4° C. and re-suspended again to ~$2 \times 10^7$/ml in the above medium pre-warmed to 37° C., with goat anti-mouse IgG antibody added to 10 mg/ml to cross-link the OKT3 bound to the TCR in the stimulated cell samples. Control cells were prepared in parallel identically, but antibodies were omitted. Following incubation for 2 min at 37° C., samples were again spun down at 4° C., washed one time with ice-cold phosphate buffered saline (Gibco BRL) and spun down at 4° C. one final time prior to cell lysis.

RAFTs were purified essentially as described previously (Zhang et al. *Immunity*, 9:239 (1998)). Cells (typically $1 \times 10^8$) were lysed at ~$3.3 \times 10^7$ cells/ml on ice by dounce homogenization (20 strokes) in 25 mM Tris pH 7.5, 150 mM NaCl, 10 mM β-glycerophosphate, 5 mM EDTA, 1% Triton X-100, 1 mM $Na_3VO_4$, 1 mM phenylmethylsulfonyl fluoride, 10 mg/ml soybean trypsin inhibitor, 2 mg/ml leupeptin, 1 mg/ml aprotinin and 1 ml aliquots of lysate were mixed with 1 ml of 80% sucrose in MNE buffer (25 mM morpholino-ethane sulfonic acid pH 6.5, 150 mM NaCl, 5 mM EDTA). Sucrose density step gradients were layered with 2 ml cell lysate/40% sucrose, 2 ml 30% sucrose in MNE buffer and finally 1 ml 5% sucrose in MNE buffer and the raft fraction isolated by ultracentrifugation (16–18 h, 4° C., 200,000 xg). The low-density, triton-insoluble raft-containing fraction (at the 5%/30% sucrose interface) was harvested and further diluted with MNE buffer, and the rafts pelleted by additional ultra-centrifugation (4 h, 4° C., 200,000 xg). Raft membrane and protein pellets were solubilized in either 1) 70% formic acid that contained cyanogen bromide (CNBr) in a molar excess over the number of methionines or 2) SDS-loading buffer for SDS-PAGE analyses. The CNBr reaction was allowed to proceed overnight in the dark. Homo-serine lactone was converted to homo-serine by hydrolysis/lyophilization using a 10-volume excess of water that also removed by-products (Goodlett, et al. 1991). After buffer exchange with 50 mM $NH_4HCO_2$ to raise the pH to approximately 8.0, smaller peptides were generated by incubation with trypsin (Promega) overnight at 37° C. at an enzyme:substrate ratio of 1:100 (w/w). To complete the preparation of the sample produced by CNBr and trypsin digestion for LC/MS/MS analysis samples were concentrated to ~5 mL and then diluted in 0.1% acetic acid. CNBr solutions were prepared fresh daily as required by addition of one crystal of CNBr to 1 mL of 70% formic acid. SDS-PAGE analysis was performed to monitor the raft preparations via silver staining of the proteins allowing observation of gross differential accumulation of proteins in the membrane raft domains between stimulated and un-stimulated cells. SDS-PAGE was not used as a preparative method for MS analysis in this study.

Isolated lipid raft pellets from both OKT3 stimulated and control Jurkat T-cells were dissolved in 70% formic acid containing cyanogen bromide (CNBr) in a molar excess over the estimated total number of methionines. The use of formic acid as a solvent allowed membrane proteins to be easily solubilized as judged by the lack of a pellet in the centrifuge tube after addition of formic acid, and simultaneously cleaved the proteins by CNBr at methionine. The resultant solution of peptides, now more soluble than the parent membrane proteins, was buffer exchanged to increase the pH and incubated with trypsin to produce smaller peptides. The resultant peptides were then esterified using either d0-or d3-methanol as described in Example I. After esterification, equal amounts of protein from stimulated (d3-methyl esterification) and un-stimulated (d0-methyl esterification) raft preparations were mixed and analyzed by microcapillary LC/MS/MS. The direct LC/MS/MS analysis of such a complex mixture of peptides resulted in identification of the most abundantly expressed proteins because of the top down data dependent approach used for ion selection. Analysis of selected proteins from the mixture indicated that there was no difference in expression between these high abundance proteins in treated and control lipid rafts (Table 1). Of the high abundance proteins identified in Table 1, only myosin appeared to change in expression on stimulation with OKT3. However, only two peptides from myosin were identified and while both generated tandem mass spectra that identified the parent protein as myosin, only one had a signal to noise level that allowed a ratio to be calculated. In another study (data not shown) one protein, Gi γ5, was not observed when proteins in the lipid raft pellet were separated by SDS-PAGE, silver stained for visualization, distinct protein bands cut out, digested with trypsin in situ and proteins identified by tandem mass spectrometry of peptides and database searching. With a molecular weight of 7318 daltons, the protein Gi γ5, might not have been retained on the polyacrylamide gel, but was identified by the approach described herein. Additionally, this protein contains only two cysteines, one of which is post-translationally modified by geranylation (Ray, et al. 1995), which points to one benefit of esterification over alkylation at cysteine for the purpose of quantifying proteins. The other Gi γ5 cysteine residue occurs in a large tryptic polypeptide that might not elute from a C18 column.

EXAMPLE III

Use of Ouantitation Data for De-Novo Sequencing

This example shows how data generated for quantitation studies can be used to generate de novo sequence. The tandem mass spectra for pairs of $[M+2H]^{2+}$ polypeptide ions differentially esterified with d0- or d3-methanol can be compared to determine fragment ion directionality by virtue of the label specific to the carboxyl-terminus. The method described here for de novo sequence derivation first compared tandem mass spectra of d0-methylated peptides to d3-methylated peptides to find those with a polypeptide mass difference within a reasonable range, corresponding to 1–5 methylesters per peptide. Such pairs were subjected to de novo polypeptide sequencing to generate a set of top sequences along with their computed scores. De novo sequence generation was aided by comparison of tandem mass spectra to remove noise, as well as b-ion fragments lacking aspartic and/or glutamic acid residues. This reduction in noise is particular advantageous when using low resolution mass spectrometric data as was done in this case. In addition, the number of methyl esters located to specific y-ions, given by an integer n, adds a useful constraint for subsequent de novo sequencing.

FIG. 2 shows a doubly charged tandem mass spectrum for a d0- and d3-methyl-esterified polypeptide pair with y-ion fragments annotated. It is evident that corresponding y-ion fragments have a mass that is heavier by $\Delta=n\delta$ in the spectrum of the d3-methanol treated sample relative to that of the d0-methanol treated sample, where n is the number of methyl esters in the corresponding polypeptide fragment (one for the C terminus and one for each aspartic or glutamic acid residue), and δ is the mass difference between the d3- and d0-methyl group (3 Da). This property can be exploited to remove noise in the spectra, as well as peaks due to b-ions lacking aspartic and/or glutamic acid residues.

Figure 3:
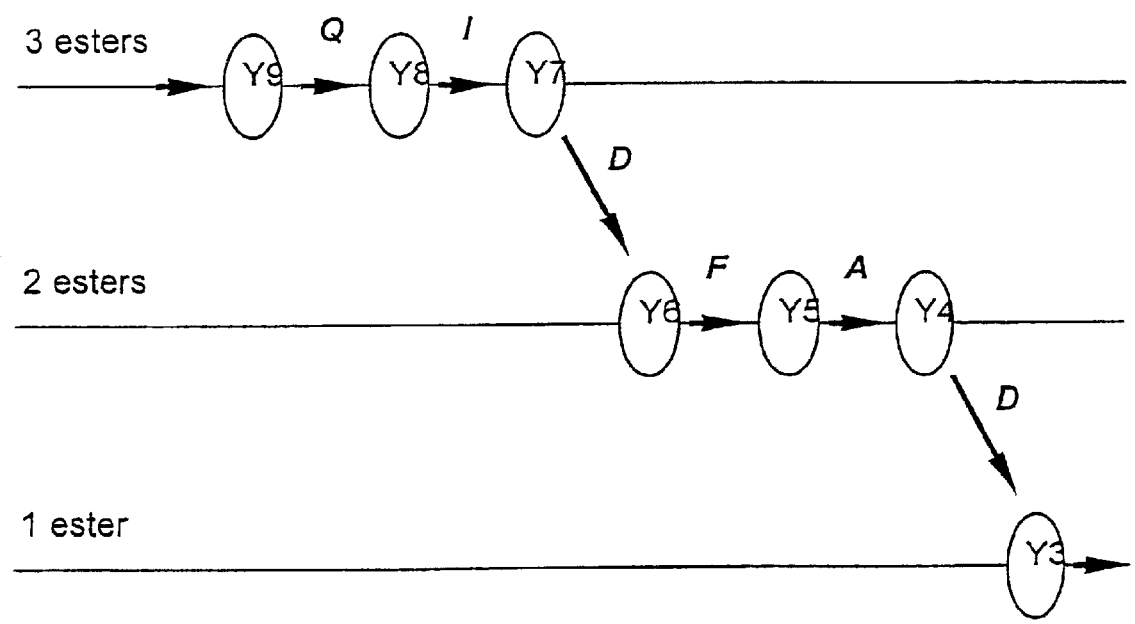
FIG. 3 shows a schematic of de novo sequence algorithm process for GNLQIDFADPSR (SEQ ID NO: 11).

The duty cycle of the ion trap during LC/MS/MS allows acquisition of a set of tandem mass spectra for d0-/d3-methylated $[M+2H]^{2+}$ ion peptides, and sufficient d0-/d3-methylated $[M+2H]^{2+}$ ion peptides pairs were present in the dataset to test the algorithm. The algorithm was applied to eight pairs of doubly charged CID spectra to from d0- and d3-methyl-esterified samples for which SEQUEST had assigned the same peptide with high confidence (Table 1). An idealized spectrum graph demonstrating how the algorithm works is illustrated in FIG. 3 for a peptide from GB01_HUMAN in Table 1. Nodes in the graph with number of esters, n, are created for each peak mass in the d0-methyl-esterified sample spectrum for which there is also

TABLE 1

Relative Abundance and Sequence of Select $[M + 2H]^{2+}$ ions

| d0-/d3-ester | Parent Protein | Database Sequence | NO: | de novo sequence | NO: |
|---|---|---|---|---|---|
| 1.0:1.0 | VIME_HUMAN | QDVDNASLAR | 1 | QDVDNAS- | 2 |
| | | QQYESVAAK | 3 | QQYESVAAK | 3 |
| 1.0:1.1 | ACTA_HUMAN | QEYDESGPSIVHR | 4 | QEYDESGP- | 5 |
| | | AGFAGDDAPR | 6 | AGFAGDDAPR | 6 |
| | | SYELPDGQVITIGNER | 7 | -PDNAVITIG- | 8 |
| 1.0:1.2 | GB01_HUMAN | LLLLGAGESGK | 9 | LLLLGAGE- | 10 |
| | | GNLQIDFADPSR | 11 | -IDFAD- | 12 |
| 1.0:1.7* | MYSN_HUMAN | DLEAHIDSANK | 13 | DLEAHID- | 14 |

*Not an average.
NO: indicates sequence identification number (SEQ ID NO:)

a peak of increased mass, nδ, in the d3-methyl-esterified sample spectrum, where δ is the mass difference between d0- and d3-methanol. Edges labeled with non-esterified amino acids, shown as horizontal arrows, are placed between the nodes with the same numbers of esters if the mass difference between the nodes corresponds to the mass of amino acid, within experimental measurement error. Similarly, edges labeled with esterified amino acids such as aspartic and glutamic acids, shown as diagonal arrows red, are placed between nodes with number of esters differing by 1 if their mass difference corresponds to the mass of the esterified amino acid. The de novo peptide sequence is then derived from the labels of the edges along the highest scoring path through the graph.

Briefly, a graphical representation (Dancik, et al. *J. Comput. Biol.*, 6:327 1999) was used to derive polypeptide sequence de novo from a pair of doubly charged CID spectra of d0- and d3-methyl-esterified peptides. Given the mass difference between the d0- and d3-methyl group δ, specified measurement uncertainty $\epsilon$, and a polypeptide of known total mass M and total number of methyl esters N, the following automated procedure was applied. First the locally low intensity peaks from both spectra to was filtered to reduce noise. Next a directed acyclic graph was constructed with the following nodes and edges. For integer values of n ranging from 1 to N, create a node with mass, m and number of methyl esters, n if there are peaks with mass m in the d0 spectrum and mass m+nδ±$\epsilon$ in the d3 spectrum. Assign this node an intensity value equal to the product of the intensities of those 2 peaks. In addition, create a single source node with m=M and n=N, and a single terminus node with m=0 and n=1.

For the edges, add a labeled weighted directed edge from node 1 $(m_1, n_1)$ to node 2 $(m_2, n_2)$ if $m_1 = m_2 +$ mass [non-methylated amino acid(s)]±$\epsilon$ and $n_1 = n_2$ or $m_1 = m_2 +$ mass [aspartic or glutamic acid methyl ester]±$\epsilon$ and $n_1 = n_2 + 1$. Assign this edge a label corresponding to the satisfying amino acid(s) and a weight equal to the product of the two node intensities. Next find the highest scoring path through the graph from the source node to the terminus node, where the score of a path is computed as the sum of the weights of its edges.

The de novo sequence of the polypeptide is given by (from carboxyl to amino-terminus) the labels of the edges of the highest scoring path. This sequence can be degenerate since some amino acids have masses within measurement uncertainty of one another. One can additionally derive a more comprehensive set of possible sequences by computing a designated number of top scoring paths.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of determining amino acid sequence of a polypeptide, comprising:
   (a) constructing a graph from mass spectra of two or more differentially labeled polypeptides, said graph comprising a node with mass m, number of labels n, intensity i, and mass differential of labels d;
   (b) creating a node corresponding to a paired signal having masses of about m and about m+nd,
   (c) adding a labeled weighted directed edge to said graph between any two nodes corresponding to a mass of an amino acid, said labeled weighted directed edge combining properties of said paired signals, and
   (d) assigning a satisfying amino acid to two or more of said labeled weighted directed edges, thereby determining said amino acid sequence.

2. The method of claim 1, wherein step (b) further comprises:
   (i) creating a source node with total mass M, total number of labels N and fixed intensity Is; and
   (ii) creating a terminus node with mass 0, minimum number of labels $n_0$, and fixed intensity $I_t$.

3. The method of claim 2, wherein step (b) further comprises (iii) selecting a path from the source node to the terminus node. node.

4. The method of claim 3, further comprising computing a priority score for each path through the graph.

5. The method of claim 1, wherein said differential label marks an internal amino acid residue.

6. The method of claim 1, wherein said differential label marks a terminal amino acid residue.

7. The method of claim 1, wherein said differential label marks a terminal and an internal amino acid residue.

8. The method of claim 1, wherein said differentially labeled polypeptides further comprise stable isotopic labels.

9. The method of claim 1, wherein said differentially labeled polypeptides further comprise heavy and light labeled isotopes selected from the group consisting of hydrogen, carbon, oxygen, nitrogen, sulfur and selenium.

10. The method of claim 1, wherein said differentially labeled polypeptides further comprise an unlabeled polypeptide and a labeled polypeptide.

11. The method of claim 1, wherein said polypeptide is labeled in vivo or in vitro.

12. The method of claim 1, wherein said mass spectra are obtained from a mass spectrometry database.

13. The method of claim 1, wherein said mass spectra are of low resolution.

14. The method of claim 1, further comprising masses of amino acid post-translational modifications.

15. The method of claim 1, further comprising adding complement node with mass M−m, and a number of labels N−n+$n_0$.

16. The method of claim 1, further comprising including multiple amino acid edges between nodes, said multiple amino acid edges characterizing a degenerate amino acid residue in said polypeptide sequence.

17. The method of claim 1, wherein steps a–c are repeated one or more times.

18. The method of claim 1, wherein steps a–c are performed by an automated process.

19. A method of determining an amino acid sequence of a polypeptide, comprising:
   (a) differentially labeling two or more polypeptide mixtures, and
   (b) determining an amino acid sequence of a polypeptide within said mixture using the method of claim 1.

20. The method of claim 19, wherein said differential label marks an internal amino acid residue.

21. The method of claim 19, wherein said differential label marks a terminal amino acid residue.

22. The method of claim 19, wherein said differential label marks a terminal and an internal amino acid residue.

23. The method of claim 19, wherein said differentially labeled polypeptides further comprise stable isotopic labels.

24. The method of claim 19, wherein said differentially labeled polypeptides further comprise heavy and light labeled isotopes selected from the group consisting of hydrogen, carbon, oxygen, nitrogen, sulfur and selenium.

25. The method of claim 19, wherein said differentially labeled polypeptides further comprise an unlabeled polypeptide and a labeled polypeptide.

26. The method of claim 19, wherein said polypeptide is labeled in vivo or in vitro.

27. The method of claim 19, wherein said mass spectra are obtained from a mass spectrometry database.

28. The method of claim 19, wherein said mass spectra are of low resolution.

29. The method of claim 19, further comprising separating components of said mixture.

* * * * *